US009339586B2

(12) United States Patent
Dankers et al.

(10) Patent No.: US 9,339,586 B2
(45) Date of Patent: *May 17, 2016

(54) MODULAR BIORESORBABLE OR BIOMEDICAL, BIOLOGICALLY ACTIVE SUPRAMOLECULAR MATERIALS

(71) Applicant: SupraPolix B.V., Eindhoven (NL)

(72) Inventors: Patricia Yvonne Wilhelmina Dankers, Helmond (NL); Gaby Maria Leonarda van Gemert, Roermond (NL); Henricus Marie Janssen, Eindhoven (NL); Egbert Willem Meijer, Waalre (NL); Anton Willem Bosman, Eindhoven (NL)

(73) Assignee: SupraPolix B.V., Eindhoven (NL)

( * ) Notice: Subject to any disclaimer, the term of this patent is extended or adjusted under 35 U.S.C. 154(b) by 0 days.

This patent is subject to a terminal disclaimer.

(21) Appl. No.: 14/527,690

(22) Filed: Oct. 29, 2014

(65) Prior Publication Data
US 2015/0057237 A1   Feb. 26, 2015

Related U.S. Application Data

(62) Division of application No. 11/913,470, filed as application No. PCT/NL2006/050107 on May 3, 2006, now Pat. No. 8,883,188.

(60) Provisional application No. 60/679,671, filed on May 11, 2005.

(30) Foreign Application Priority Data

May 4, 2005   (EP) ..................... 05103764
Nov. 21, 2005 (EP) ..................... 05111018

(51) Int. Cl.
A61L 27/18   (2006.01)
A61L 27/58   (2006.01)
A61L 31/06   (2006.01)
C08G 83/00   (2006.01)
C08G 18/48   (2006.01)
C08G 18/67   (2006.01)
C08G 18/73   (2006.01)
C08G 18/42   (2006.01)
A61L 27/34   (2006.01)

(52) U.S. Cl.
CPC ............... *A61L 27/18* (2013.01); *A61L 27/34* (2013.01); *A61L 27/58* (2013.01); *A61L 31/06* (2013.01); *C08G 18/4202* (2013.01); *C08G 18/4238* (2013.01); *C08G 18/4277* (2013.01); *C08G 18/4833* (2013.01); *C08G 18/672* (2013.01); *C08G 18/73* (2013.01); *C08G 83/008* (2013.01); *A61L 2300/216* (2013.01); *A61L 2300/224* (2013.01); *A61L 2300/236* (2013.01); *A61L 2300/25* (2013.01); *A61L 2420/06* (2013.01); *Y10S 623/916* (2013.01)

(58) Field of Classification Search
None
See application file for complete search history.

(56) References Cited

U.S. PATENT DOCUMENTS

| 3,375,800 A | 4/1968 | Cole et al. |
| 3,388,087 A | 6/1968 | Dieterich et al. |
| 3,480,592 A | 11/1969 | Dieterich et al. |
| 4,093,759 A | 6/1978 | Otsuki et al. |
| 4,136,092 A | 1/1979 | Jackle et al. |
| 4,140,759 A | 2/1979 | Mausner |
| 4,216,318 A | 8/1980 | Brown et al. |
| 4,229,838 A | 10/1980 | Mano |
| 4,322,327 A | 3/1982 | Yoshimura et al. |
| 4,684,728 A | 8/1987 | Mohring et al. |
| 4,942,035 A | 7/1990 | Churchill et al. |
| 5,410,016 A | 4/1995 | Hubbell et al. |
| 5,500,209 A | 3/1996 | Mendolia et al. |
| 5,548,035 A | 8/1996 | Kim et al. |
| 5,610,268 A | 3/1997 | Meijer et al. |
| 5,631,337 A | 5/1997 | Sassi et al. |
| 5,723,563 A | 3/1998 | Lawrey et al. |
| 5,736,535 A | 4/1998 | Bernstein et al. |
| 5,874,069 A | 2/1999 | Mendolia et al. |
| 5,883,211 A | 3/1999 | Sassi et al. |
| 5,919,441 A | 7/1999 | Mendolia et al. |

(Continued)

FOREIGN PATENT DOCUMENTS

EP   0 259 92 B1   9/1983
EP   0 433 188 A1  6/1991

(Continued)

OTHER PUBLICATIONS

Brunsveld et al., "Supramolecular Polymers," Chemical Reviews, 101:4071-4097 (2001).

(Continued)

Primary Examiner — Dennis Heyer
(74) Attorney, Agent, or Firm — Foley & Lardner LLP; Sunit Talapatra

(57) ABSTRACT

The present invention relates to a modular supramolecular bioresorbable or biomedical material comprising (i) a polymer comprising at least two 4H-units and (ii) a biologically active compound. Optionally, the supramolecular bioresorbable or biomedical material comprises a bioresorbable or biomedical polymer as third component to tune its properties (mechanical and bioresorption properties). The supramolecular bioresorbable or biomedical material is especially suitable for biomedical applications such as controlled release of drugs, materials for tissue-engineering, materials for the manufacture of a prosthesis or an implant, medical imaging technologies.

13 Claims, 2 Drawing Sheets

(56) References Cited

U.S. PATENT DOCUMENTS

| | | | |
|---|---|---|---|
| 6,320,018 | B1 | 11/2001 | Sijbesma et al. |
| 6,353,076 | B1 | 3/2002 | Barr et al. |
| 6,489,397 | B2 | 12/2002 | Kim et al. |
| 6,534,072 | B2 | 3/2003 | Mondet et al. |
| 6,683,151 | B1 | 1/2004 | Loontjens et al. |
| 6,702,850 | B1 | 3/2004 | Byun et al. |
| 6,716,370 | B2 | 4/2004 | Kendig |
| 6,743,767 | B2 | 6/2004 | Goldoni et al. |
| 6,803,447 | B2 * | 10/2004 | Janssen et al. ............ 528/423 |
| 6,803,477 | B2 | 10/2004 | Prakash et al. |
| 6,818,018 | B1 | 11/2004 | Sawhney |
| 6,899,992 | B2 | 5/2005 | Huang et al. |
| 6,911,296 | B2 | 6/2005 | Pappas et al. |
| 6,939,938 | B2 | 9/2005 | Benard et al. |
| 6,972,304 | B2 | 12/2005 | Smith et al. |
| 7,196,073 | B2 | 3/2007 | Marciani |
| 7,622,131 | B2 | 11/2009 | Bosman et al. |
| 7,736,663 | B2 | 6/2010 | Cooper et al. |
| 7,838,621 | B2 | 11/2010 | Janssen et al. |
| 7,862,805 | B2 | 1/2011 | Mougin et al. |
| 2001/0053377 | A1 | 12/2001 | Mondet et al. |
| 2003/0013631 | A1 | 1/2003 | Goldoni et al. |
| 2003/0015185 | A1 | 1/2003 | Dutart |
| 2003/0019391 | A1 | 1/2003 | Kendig |
| 2003/0079644 | A1 | 5/2003 | Smith et al. |
| 2003/0092838 | A1 | 5/2003 | Fomperie et al. |
| 2003/0129506 | A1 | 7/2003 | Pappas et al. |
| 2003/0158403 | A1 | 8/2003 | Manoharan et al. |
| 2003/0166822 | A1 | 9/2003 | Benard et al. |
| 2004/0023155 | A1 | 2/2004 | Hayakawa et al. |
| 2004/0034190 | A1 | 2/2004 | Janssen et al. |
| 2004/0087755 | A1 | 5/2004 | Eling et al. |
| 2004/0091812 | A1 | 5/2004 | Huang et al. |
| 2004/0161394 | A1 | 8/2004 | Mougin et al. |
| 2004/0220142 | A1 | 11/2004 | Marciani |
| 2005/0031566 | A1 | 2/2005 | Cooper et al. |
| 2007/0093639 | A1 | 4/2007 | Jassen et al. |
| 2007/0149751 | A1 | 6/2007 | Lindsay et al. |
| 2007/0264208 | A1 | 11/2007 | Mougin et al. |
| 2008/0260795 | A1 | 10/2008 | Baughman et al. |
| 2009/0004274 | A1 | 1/2009 | Hoorne-Van Gemert et al. |
| 2009/0111930 | A1 | 4/2009 | Hoorne-Van Gemert et al. |
| 2009/0130172 | A1 | 5/2009 | Dankers et al. |
| 2010/0076147 | A1 | 3/2010 | Hoorne-Van Gemert et al. |
| 2011/0034641 | A1 | 2/2011 | Janssen et al. |
| 2011/0229724 | A1 | 9/2011 | Hoorne-Van Gemert et al. |
| 2012/0116014 | A1 | 5/2012 | Janssen et al. |

FOREIGN PATENT DOCUMENTS

| | | |
|---|---|---|
| EP | 0 683 769 B1 | 11/1995 |
| EP | 0 744 428 A2 | 11/1996 |
| EP | 0 877 055 B1 | 11/1998 |
| EP | 1 213 309 A1 | 6/2002 |
| EP | 1 687 378 A1 | 8/2006 |
| EP | 1 310 533 B2 | 1/2007 |
| EP | 1 392 222 B1 | 9/2007 |
| EP | 2 450 394 A1 | 5/2012 |
| FR | 2657082 A1 | 7/1991 |
| FR | 2825628 B1 | 12/2002 |
| JP | 48-029398 B | 9/1973 |
| JP | 51-022823 A | 2/1976 |
| JP | 52-074692 A | 6/1977 |
| JP | 2004-250623 A | 9/2004 |
| SU | 910718 A1 | 3/1982 |
| WO | WO-98/14504 A1 | 4/1998 |
| WO | WO-98/14505 A1 | 4/1998 |
| WO | WO-98/23307 | 6/1998 |
| WO | WO-99/07343 A1 | 2/1999 |
| WO | WO-01/44307 A2 | 6/2001 |
| WO | WO-02/34312 A1 | 5/2002 |
| WO | WO-02/46260 A1 | 6/2002 |
| WO | WO-02/098377 A1 | 12/2002 |
| WO | WO03/032929 * | 4/2003 ............ A61K 7/06 |
| WO | WO-03/032929 A2 | 4/2003 |
| WO | WO-03/059964 A2 | 7/2003 |
| WO | WO-03/099875 A2 | 12/2003 |
| WO | WO-2004/016598 A1 | 2/2004 |
| WO | WO-2004/052963 A1 | 6/2004 |
| WO | WO-2005/042641 A1 | 5/2005 |
| WO | WO-2006/006855 A1 | 1/2006 |
| WO | WO-2006/118460 A1 | 11/2006 |
| WO | WO-2006/118461 A2 | 11/2006 |
| WO | WO-2007/058539 A2 | 5/2007 |
| WO | WO-2007/072000 A1 | 6/2007 |
| WO | WO-2008/063057 A3 | 5/2008 |
| WO | WO-2010/002261 A1 | 1/2010 |
| WO | WO-2010/002262 A1 | 1/2010 |

OTHER PUBLICATIONS

Cate et al., "Hydrogen-Bonded Supramolecular Polymers with Tunable Material Properties," Polymer Preprints, 44(1):618-619 (2003).
Chemical Abstract, vol. 85, Abst. No. 15348y, Jul. 1976, 1 Page.
Chemical Abstracts, vol. 80, No. 20, May 20, 1974, English abstract of JP 04 829398, filed Aug. 28, 1968, 1 Page.
Chemical Abstracts, vol. 97, No. 10, Sep. 1982, Veselovskii et al., "Adhesive Composition," Inst. of the Chemistry of High Molecular Weight Compounds, Mar. 5, 1979, 1 Page.
Derwent 91-179975125, 1 Page.
Derwent Abstract Acc. No. 1977-55084Y, Week 197731, English abstract for JP 52-74692, Jun. 22, 1977, 3 pages.
Dieterich et al, "Polyurethane Ionomers, a New Class of Block Polymers," Angewandte Chemie Intternational Edition, 9(1):40-50 (1970) (English version of German article in Angewandte Chemie, 2:40-50 (1970).
El-Ghayoury et al., "Supramolecular Hydrogen-Bonded Oligo(p-phenylene vinylene) Polymers," Angewandte Chemie International Edition, 40(19):3660-3663 (2001).
Even et al., "Synthesis and Characterization of Amphiphilic Triblock Polymers by Copper Mediated Living Radical Polymerization," European Polymer Journal, 39:633-639 (2003).
Flory, "Random Reorganization of Molecular Weight Distribution in Linear Condensation Polymers," Journal of American Chemical Society, 64:2205-2212 (1942).
Folmer et al., "Supramolecular Polymer Materials: Chain Extension of Telechelic Polymers Using a Reactive Hydrogen-Bonding Synthon," Advanced Materials, 12(12):874-878 (2000).
Guan et al., "Modular Domain Structure: A Biomimetic Strategy for Advanced Polymeric Materials," Journal of American Chemical Society, 126:2058-2065 (2004).
Guan et al., "Synthesis and Single-Molecule Studies of Modular Polymers Using Precise Hydrogen Bonding Interactions," Polymer Preprints, 44(2):485-486 (2003).
Hirschberg et al., "Helical Supramolecular Aggregates Based on Ureidopyrimidinone Quadruple Hydrogen Bonding," Chemistry—A European Journal, 9:4222-4231 (2003).
Hirschberg et al., "Supramolecular Polymers from Linear Telechelic Siloxanes with Quadruple-Hydrogen-Bonded Units," Macromolecules, 32(8):2696-2705 (1999).
Hirschberg et al., "Ureidotriazine-Based Supramolecular Copoloymers," Marcomolecules, 36:1429-1432 (2003).
Hofmeier et al., "New Supramolecular Polymers Containing Both Terpyridine Metal Complexes and Quadruple Hydrogen Bonding Units," Chemical Communications, 318-319 (2004).
International Preliminary Report on Patentability in PCT/NL2009/050401 dated Jan. 5, 2011.
International Search Report dated Mar. 1, 2004 for PCT/NL03/00766.
International Search Report mailed Aug. 14, 2009 in International Application No. PCT/NL2009/050401.
International Search Report mailed Oct. 24, 2005 for PCT/NL2005/000497, 3 pages.
International Search Report, PCT/NL03/00870 dated Apr. 2, 2004.
International Search Report, PCT/NL2006/050106, mailed Aug. 29, 2006, 4 Pages.
International Search Report, PCT/NL2006/050107, mailed Jul. 12, 2007, 3 pgs.

(56) References Cited

OTHER PUBLICATIONS

International Search Report, PCT/NL2006/050562, mailed Nov. 24, 2008, 3 pages.
International Search Report, PCT/NL2009/050401 dated Aug. 14, 2009.
Kato, "Supramolecular Liquid Crystal Polymers, Formation of Molecular Self-Organized Structures and Their Functionalization," Kobunshi Ronbunshu, 54(12):855-862 (1997). (Abstract on last page).
Kautz et al., "Cooperative End-to-End and Lateral Hydrogen-Bonding Motifs in Supramolecular Thermoplastic Elastomers," Macromolecules, 39:4265-4267 (2006).
Kiriy et al., "Atomic Force Microscopy Visualization of Single Star Copolymer Molecules," Polymeric Materials: Science & Engineering, 88:233-234 (2003).
Korshak et al., "Experimental Methods of Bulk Polymerization," Comprehensive Polymer Science: The Synthesis, Characterization, Reactions & Application of Polymers, 5:131-142 (1989).
Lange et al., "Hydrogen-Bonded Supramolecular Polymer Networks," Journal of Polymer Science, Polymer Chemistry Edition, Interscience Publishers, 37:3657-3670 (1999).
Lange et al., "Supramolecular Polymer Interactions Based on the Alternating Copolymer of Styrene and Maleimide," Macromolecules, 28:782-783 (1995).
Lee et al., "Hydrogels for Tissue Engineering," Chemical Reviews, 101(7):1869-1879 (2001).
Matsuda et al., "Terminally Alkylated Heparin. 1. Antithrombogenic Surface Modifier," Biomacromolecules, 2:1169-1177 (2001).
Maynard et al., "Inhibition of Cell Adhesion to Fibronectin by Oligopeptide-Substituted Polynorbornenes," Journal of American Chemical Society, 123:1275-1279 (2001).
Menger et al., "Self-Adhesion Among Phospholipd Vesicles," Journal of the American Chemical Society, 128:1414-1415 (2006).
Rieth et al., "Polymerization of Ureidopyrimidinone-Functionalized Olefins by Using Late-Transition Metal Ziegler-Natta Catalysts: Synthesis of Thermoplastic Elastomeric Polyolefins," Angewandte Chemie International Edition, 40(11):2153-2156 (2001).
Roland et al., "Synthesis of Titin-Mimicking Polymers Having Modular Structures by Using Noncovalent Interactions," Polymer Preprints, 44(1):726-727 (2003).
Rowley et al., "Alginate Hydrogels as Synthetic Extracellular Matrix Materials," Biomaterials, 20:45-53 (1999).
Saunders et al. (editors), "Polyurethanes—Chemistry and Technology High Polymers: Part 1. Chemistry," High Polymers, Interscience Publishers a Division of Wiley & Sons, 26(1):68-73 (1962).
Sijbesma et al., "Reversible Polymers Formed from Self-Complementary Monomers Using Quadruple Hydrogen Bonding," Science, 278:1601-1604 (1997).
Uhrich et al., "Polymeric Systems for Controlled Drug Release," Chemical Reviews, 99:3181-3198 (1999).
Urbanski et al. "Potential Antimalarial Compounds. IX. Pyrimidine Derivatives of Urea and Guanidine," Journal of Medicinal Chemistry, 10:521-525 (1967).
Vulic et al., "Heparin-Containing Block Copolymers," Journal of Materials Science: Materials Medicine, 4:353-365 (1993).
Weast et al. (editors), "CRC Handbook of Chemistry & Physics, 59th Edition," CRC Press, Inc., 3 pages (1978-1979).
Yamauchi et al., "Thermoreversible Poly(alkyl acrylates) Consisting of Self-Complementary Multiple Hydrogen Bonding," Macromolecules, 36:1083-1088 (2003).
Yamauchi et al., Abstract of "Synthesis and Characterization of Novel Multiple-Hydrogen Bonded Macromolecules via a Michael Reaction," Dept. of Chemistry, Virginia Polytechnic Institute and State University, 1 page.
Yamauchi, et al., "Thermoreversible Polyesters Consisting of Multiple Hydrogen Bonding (MHB)," Macromolecules, 37(10):3519-3522 (2004).
Product Information—Isocytosine—, Product No. I 2127, SIGMA (Jan. 2004).

* cited by examiner

MODULAR BIORESORBABLE OR BIOMEDICAL, BIOLOGICALLY ACTIVE SUPRAMOLECULAR MATERIALS

CROSS-REFERENCE TO RELATED APPLICATION(S)

This application is a Divisional of U.S. application Ser. No. 11/913,470, filed Nov. 2, 2007 as the National Phase of International Patent Application No. PCT/NL2006/050107, filed May 3, 2006, published as WO 2006/118461. PCT/NL2006/050107 claims priority to European Application No. 05 111 018.7, filed Nov. 21, 2005, European Application No. 05 103 764.6, filed May 4, 2005, and Provisional Application No. 60/679,671, filed May 11, 2005. The contents of these applications are herein incorporated by reference in their entirety.

FIELD OF THE INVENTION

The invention relates to new supramolecular bioresorbable or biomedical materials that are biologically active, as well as to a process to prepare such bioresorbable or biomedical materials in a supramolecular and/or modular way, in order to obtain materials that allow easy fine-tuning of the material properties, bioresorption properties and/or bioactivity by making use of reversible supramolecular interactions. More specifically, appearance, mechanical strength, elasticity, bioresorption and bioactivity are tuned by making use of these reversible supramolecular interactions. The new materials of this invention can be used in a variety of biomedical applications that will benefit from said properties including biomedical coating compositions.

BACKGROUND OF THE INVENTION

A wide variety of bioresorbable or biomedical materials are known that are mostly based on aliphatic polyesters (Uhrich et al. Chem. Rev. 99, 3181-3198, 1999). The mechanical properties of current bioresorbable or biomedical materials are strongly related to their high molecular weights that are in general over 100 kDa, the presence of chemical cross-links, and the presence of crystalline domains in these polymers. Although the crystalline domains are beneficial for the mechanical properties of the material (strength and elasticity), they do have a strong impact on the biodegradation process of the material as the biodegradation of crystalline domains is in general very slow and crystalline domains may cause immunological responses. Moreover, the need for high molecular weight polymers, in order to get the desired material properties, usually implies that high processing temperatures are required, and these are unfavorable as thermal degradation processes become more likely, especially when biologically active species are involved.

There are also several examples of biologically active species that have been covalently attached to polymers for biomedical uses. Especially, oligo-peptide based cell-adhesion promoters such as RGD-sequences have had considerable attention in this respect. RGD-peptides have been covalently attached to a synthetic polymer by copolymerizing RGD-containing monomers, in order to obtain biologically active polynorbornenes (Grubbs et al., J. Am. Chem. Soc. 123, 1275, 2001). Unfortunately, in this way it was only possible to obtain biologically active polynorbornenes, a polymer that is not bioresorbable, and one needs complex chemistry to change the specific biofunctionality. As a result, one is limited in the amount and choice of (combinations) of biologically active molecules. Consequently, this approach lacks freedom in the choice of polymers and bioactivities.

The biologically active RGD-sequence has also been covalently attached to alginates, a naturally occurring polysaccharide (Mooney et al., Biomaterials 20, 45, 1999). The resulting hydrogel materials show enhanced proliferation of myoblast cells. However, specific carbodiimide chemistry is needed to introduce the bioactivity and only materials based on alginates can be used, thereby limiting the mechanical and bioresorbable or biomedical properties of the resulting material. Moreover, polymers from natural sources, such as polysaccharides, are generally costly and may show quality differences when different batches are compared. As the production of synthetic polymers is more controlled, synthetic polymers are preferred because a constant quality can be ensured.

Further known in the art are biomedical coatings that are used to improve the biocompatibility of medical devices. For example, stents may be coated to reduce thrombosis (cf. for example U.S. Pat. No. 6,702,850, incorporated by reference) and implants may be coated to reduce the risks of rejection. Biomedical coatings may further comprise biologically active agents that are released in a controlled manner. Such biomedical coatings may be prepared by mixing a biologically active agent with a polymeric coating formulation.

A biological active agent that has been covalently attached to several polymers for biomedical coatings are heparin-derivatives. For example heparins have been copolymerized in polystyrene and poly(ethylene glycol) systems (Feijen et al., J. Mater. Sci. Mat. Med. 4, 353, 1997), or heparins have been covalently attached to polyurethanes as disclosed in WO98/23307. These heparin-polymer conjugates are used as anti-thrombogenic coatings for structures to be introduced into living systems. In both cases aromatic diisocyanates are used that are known for their toxic biodegradation profile and a relative low amount of heparin is available at the surface of the coating resulting in a low anti-thrombogenic activity.

Although a strong anchoring of the biologically active molecules to the polymer backbone is preferred in order to guarantee strong cell-adhesion or prolonged bioactivity, there are also materials in which biologically active molecules are only mixed with polymers and are thus not covalently attached to the polymer chain. As a consequence, the biologically active molecules leak out of the material and, therefore, such materials only find uses in drug delivery applications. Examples are hydrogels and microcapsules. Unfortunately, in hydrogels, the rate of drug delivery is hard to tune, while these systems generally suffer from poor material properties. Additionally, the chemical cross-links in their structure limit their biodegradation behaviour. Microcapsules, on the other hand, are prepared from polymers with high glass-transition or melting temperatures, limiting their mechanical performance. Also, microcapsules frequently need bio-incompatible organic solvents to process them.

Another example of non-covalently attached biological active molecules are heparins that are ionically bound to cationic coatings due to heparin's intrinsic negative charge caused by the presence of carboxylates and sulfonates in the molecule, as disclosed for example in U.S. Pat. No. 4,229,838. This method is however rather limited because the bioactive compound is leached over time from the surface due to the relative low ionic binding strength.

Alternatively, hydrophobic interactions have been used to non-covalently attach heparin to polymeric surfaces by end-group functionalizing heparin with an alkyl chain (Matsuda et al., Biomacromolecules, 2, 1169, 2001). However, the hydrophobic interactions are rather poor, resulting in a fast decrease in activity due to leakage of the heparins from the polymeric surfaces.

In general, "supramolecular chemistry" is understood to be the chemistry of non-covalent, oriented, multiple (at least two), co-operative interactions. For instance, a "supramolecular polymer" is an organic compound that has polymeric properties—for example with respect to its rheological behaviour—due to specific and strong secondary interactions between the different molecules. These non-covalent supramolecular interactions contribute substantially to the properties of the resulting material.

Supramolecular polymers comprising (macro)molecules that bear hydrogen bonding units can have polymer properties in bulk and in solution, because of the H-bridges between the molecules. Sijbesma et al. (see WO 98/14504 and Science 278, 1601, 1997) have shown that in cases where the self-complementary quadruple hydrogen unit (4H-unit) is used, the physical interactions between the molecules become so strong that polymers with much better material properties can be prepared.

Several telechelic polymers have been modified with 4H-units before, as has been published in Folmer, B. J. B. et al., Adv. Mater. 12, 874, 2000, and in Hirschberg et al., Macromolecules 32, 2696, 1999. However, these polymers only contain the 4H-unit coupled at the ends of the polymer chains. Consequently, the number of 4H-units in the macromolecule is limited by the amount of end groups to two, and the functional units are always located on the periphery of the polymer, limiting the mechanical properties of the resulting materials.

WO 02/034312 discloses polymers to which heparin is covalently attached. via functional groups.

WO 02/46260 discloses polyurethane based polymers with end capped 4H-bonding units that are optionally grafted with additional 4H-bonding units. The disclosed polymers can be used as hot melt adhesive or TPU-foam. WO 02/98377 discloses a cosmetic composition for care and/or treatment and/or make-up of keratinous materials comprising in a physiologically acceptable medium an efficient amount of a polymer having functional groups that are capable to bind to other functional groups by at least three hydrogen bridges. WO 02/98377 explicitly refers to WO 98/14504 and states that WO 98/14504 does not disclose a cosmetic use of the polymers disclosed therein. WO 02/46260 and WO 02/98377 use comparable or the same chemistry as described in Folmer et al. and Hirschberg et al.

WO 2004/016598, incorporated by reference, discloses chemistry to acquire polymers with grafted quadruple H-bonding units. For example, polyacrylates and polymethacrylates with grafted 4H-units have been produced using different kinds of polymerization techniques. WO 2004/016598 further discloses that these polymers are suitable for applications related to personal care, surface coatings, imaging technologies, biomedical applications, e.g. materials for controlled release of drugs ad materials for tissue engineering and tablet formation, adhesive and sealing compositions, and thickening agents and binders.

WO 2004/052963, incorporated by reference, discloses polysiloxanes comprising 4H-units in the polymer backbone. More precisely, polysiloxanes are disclosed having (a) 4H-units directly incorporated in the polymer backbone, or (b) 4H-units pending from the polymer backbone, wherein the 4H-units are covalently attached via one linker through a silicon-carbon bond. However, the disclosed polymers are not bioresorbable.

Low molecular weight telechelic polycaprolactone end-capped with 4H-units has been described by Dankers et al. (Abstracts of Papers, 225th ACS National Meeting, New Orleans, La., United States, Mar. 23-27, 2003; see PMSE, 88, 52, 2003). It was found that films of this material were biocompatible based on the observed attachment of fibroblast cells to the films. The study on the biodegradation of this polymer showed the presence of crystallites which is not favourable for bioresorption. Moreover, in a paper by ten Cate et al. (Abstracts of Papers, 225th ACS National Meeting, New Orleans, La., United States, Mar. 23-27, 2003; see Polymer Preprints, 2003, 44(1), 618) it was shown that the elasticity of the material was rather poor, as elongations beyond 130% were not possible.

Hence there is a need for versatile supramolecular bioresorbable or biomedical materials that have good and tunable mechanical properties and/or tunable biofunctionality. Additionally, it is desired that these materials are tunable in their biodegradation behavior. Furthermore, it is desired that they can easily be prepared and processed. The present invention addresses these needs by introducing a supramolecular modular approach, wherein different ingredients (or modules or components) are blended—with each module contributing its own specific characteristic (i.e. mechanical performance, bioresorption, bioactivity, etc.)—to produce a material displaying the combined characteristics. This modular approach is usually not easily possible, but is enabled here, as quadruple hydrogen bonding units (4H-units) are used in at least one of the modules that are applied, resulting in contact between the modules in the final material. The presented approach eliminates the need for extensive covalent synthesis, as blending experiments with the various modules can be used to fine-tune the properties of the final material. In addition, every module can be prepared in a controlled way, leading to well defined structures that result in products of controllable high quality.

SUMMARY OF THE INVENTION

It is an object of the present invention to provide novel supramolecular bioresorbable or biomedical materials as well as the process to prepare such materials with the aim to obtain biomedical materials with better characteristics than those of the prior art. In particular, the supramolecular biomedical material is a supramolecular coating composition.

It is another object of the present invention to provide supramolecular bioresorbable or biomedical materials having the additional feature that they are easily fine-tuned with respect to their characteristics (e.g. mechanical properties, bioresorption, bioactivity, etc.). The present invention therefore relates to a supramolecular bioresorbable or biomedical material comprising the following components:

(a) a polymer comprising at least two 4H-units; and (b) a biologically active compound;

wherein the 4H-unit is represented by the general formulas (1) or (2):

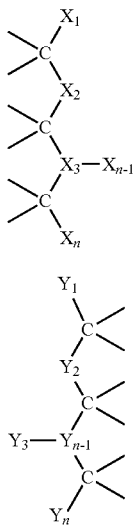

(1)

(2)

wherein the C—$X_i$ and the C—$Y_i$ linkages each represent a single or double bond, n is 4 or more, and $X_i$ represent donors or acceptors that form hydrogen bridges with the H-bridge forming monomeric unit containing a corresponding general form (2) linked to them with $X_i$ representing a donor and $Y_i$ an acceptor and vice versa. The structure of these 4H-units is in detail disclosed in WO 98/14505 which is expressly incorporated by reference.

Component (a) is preferably bioresorbable when the supra, olecualr material is bioresorbable, and according to the present invention, the terms "bioresorbable" and "bioresorption" encompasses processes such as cell-mediated degradation, enzymatic degradation and/or hydrolytic degradation of the supramolecular bioresorbable polymer, and/or elimination of the supramolecular bioresorbable polymer from living tissue as will be appreciated by the person skilled in the art.

In addition, a biologically active compound is to be understood as a cosmetically and/or pharmaceutically active compound that can induce a biological or biochemical effect in a mammal, but does not include biological systems such as cells and cell organelles.

DETAILED DESCRIPTION OF THE INVENTION

Figure 1:
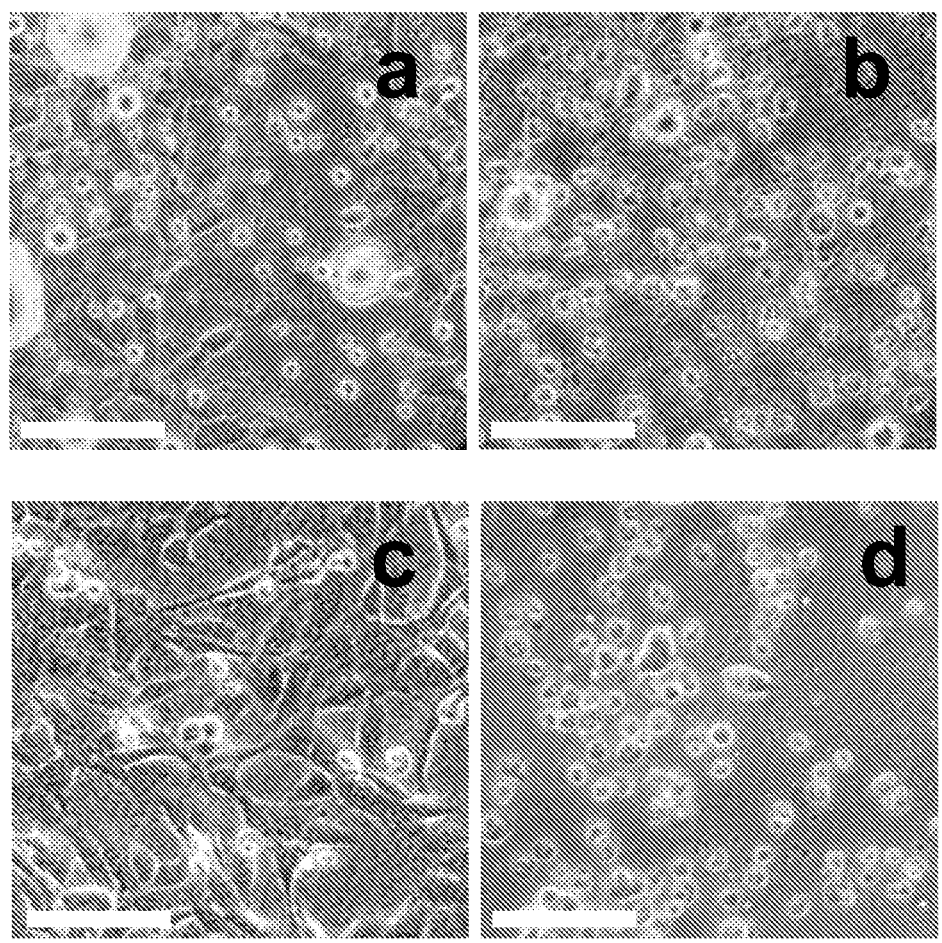
FIG. 1 shows cell adhesion and spreading in vitro. Fibroblast cell (5·104 cells/cm2) adhesion and cell spreading on different drop cast films (FIG. 1a: example 29a, FIG. 1b: example 29b, FIG. 1c: example 29c and FIG. 1d: example 14) after two days of cell culturing in the absence of FBS. In all cases 4 mole % of peptide was mixed with the polymer of example 14. The cells were visualized on the polymer films with optical microscopy; scale bars represent 100 µm.

When investigating supramolecular polymers comprising quadruple hydrogen bonding units (4H-units), it was surprisingly found that by blending different polymers, optionally modified with 4H-units, not only the mechanical properties of the blends could be modified and improved, but also their biodegradation behaviour. Moreover, biologically active compounds, optionally modified with 4H-unit(s), could be added to these materials, making the bioresorbable or biomedical material biologically or biochemically active by blending in the desired biologically active compound. This invention therefore enables the use of biologically or biochemically active materials with improved mechanical properties, while being able to tune separately the biodegradation rate and the bioactivity of the material. Thus, this invention surpasses the state of the art in biomedical materials, as a simplified way of designing and preparing new biologically active, bioresorbable or biomedical materials is introduced by using the supramolecular modular approach.

Component (a)

Accordingly, component (a), is a polymer comprising at least two 4H-units, preferably 2-50, more preferably 3-50, even more preferably 3-20, and most preferably 4-15 4H-units that are covalently attached to the polymer chain. The 4H-units may be attached at the termini of the polymer chain as well as to the backbone of the polymer chain or both. Obviously, the supramolecular bioresorbable or biomedical material of this invention may comprise more than one component (a), e.g. polymers of different chemical nature, of different molecular weight, and/or different numbers of 4H-units. It is also possible that component (a) is constituted from components of different chemical nature and/or of different molecular weight.

It is preferred that component (a) is a bioresorbable polymer. However, if the supramolecular biomedical material is a supramolecular biomedical coating composition, it may be more preferred that component (a) is not bioresorbable.

Component (a) can be any type of polymer, i.e. the polymer can be of synthetic origin or of natural origin, such as chitosan, collagen, fibrin, or proteoglycans. However, it is preferred that component (a) is selected from the group consisting of polyethers, aliphatic polyesters, aromatic polyesters, polyurethanes, polyamides, polyacrylates, polymethacrylates, polyacrylamides, (hydrogenated) polyolefins, polysiloxanes, polycarbonates, polyorthoesters, polysaccharides, poly(N-vinylcaprolactam), polyvinylpyrrolidone and polyvinylalcohols (preferably partly esterified) or copolymers from these polymers such as polyvinylpyrrolidone/vinyl acetate copolymer.

According to a more preferred embodiment of the invention, component (a) is selected from the group consisting of polyethers, aliphatic polyesters, polycarbonates, polysiloxanes and polyorthoesters. Even more preferably, component (a) is selected from the group consisting of polyethers, aliphatic polyesters and polycarbonates. Most preferably, component (a) is an aliphatic polyester.

In another more preferred embodiment of this invention, component (a) is selected from the group consisting of polyamides, polyacrylates, polymethacrylates, polyacrylamides, poly(N-vinylcaprolactam), or copolymers of these polymers.

The number average molecular weight $M_n$ of component (a) is preferably in the range from 100 to 100000, more preferably from 100 to 60000, even more preferably 800 to 40000, most preferably from 2000 to 35000 Dalton.

Preferably, component (a) is prepared from relatively low molecular weight polymers having two hydroxy end-groups, primary amino end-groups, or a combination thereof. More preferably, component (a) is prepared from relatively low molecular weight polymers having two hydroxyl end-groups. Examples of relatively low molecular weight polymers having two hydroxy end-groups are:
(i) polyether diols having a polyoxyalkylene structure and OH end-groups;
(ii) polyesters and copolyesters having OH end-groups;
(iii) polycarbonates and copolycarbonates having OH end-groups;
(iv) polyorthoesters having OH end-groups;
(v) (hydrogenated) polyolefine diols; and
(vi) polymers and copolymers based on combinations of these preferred polymers (i)-(v).

Suitable examples of polymers (i) are polyetherdiols having a polyoxyalkylene structure and OH end-groups, e.g. polyethylene glycol, polypropylene glycol, poly(ethylene-co-propylene) glycol (random or block), polytetramethylene glycol. Examples of polymers (ii) are polyesters and copolyesters made by polycondensation of dicarboxylic acids, e.g. adipic acid, and diols, e.g. 1,6-hexanediol or glycols, or by polycondensation of hydroxyacids, e.g. lactic acid; polyesters and copolyesters made by ringopening polymerisation of e.g. ε-caprolactone, glycolide, lactide, δ-valerolactone, 1,4-dioxane-2-one, 1,5-dioxepan-2-one, oxepan-2,7-dione, and the like. Examples of polymers (iii) are polycarbonates and copolycarbonates based on e.g. 1,6-hexanediol polycarbonate, polycarbonates and copolycarbonates made by ringopening polymerization of e.g. trimethylenecarbonate, 1,3-dioxepane-2-one, 1,3-dioxanone-2-one, 1,3,8,10-tetraoxacyclotetradecane-2,9-dione. An example of polymers (iv) is a polyorthoester based on e.g. 3,9-diethylene-2,4,8,10-tetraoxaspiro[5.5]undecane. Examples of polymers (v) are OH functionalized polybutadiene and OH functionalized poly(ethylene-butylene). An example of polymers (vi) are OH functionalized block copolymers of polycaprolactone and polyethyleneglycol.

Examples of relatively low molecular weight polymers having two amino end-groups are Jeffamines® (polyoxyalkylene amines produced and marketed by Huntsman), or other polyethers, aliphatic polyamides or polysiloxanes.

Preferably, the polymers have two hydroxyl end-groups, primary amine end-groups, or a combination thereof have a number average molecular weight $M_n$ of 500 to and 10000, more preferably of 750 to 7000.

According to a first preferred embodiment of the present invention, the supramolecular bioresorbable or biomedical material comprises 50.0-99.99 percent by weight of component (a) and 0.01-50.0 percent by weight of component (b) if no component (c) is present (vide infra). More preferably, the supramolecular bioresorbable or biomedical material comprises 70.00-99.99 percent by weight of component (a) and 0.01-30.00 percent by weight of component (b). Most preferably, the supramolecular bioresorbable or biomedical material comprises 90.00-99.95 percent by weight of component (a) and 0.05-10 percent by weight of component (b). All these weight ranges are based on the total weight of the supramolecular bioresorbable or biomedical material.

Component (a) may have all kinds of different architectures, e.g. a linear (co)polymer with the 4H-units attached to it as end groups, and/or in the polymer backbone, and/or grafted onto the polymer chain; a star shaped (co)polymer with the 4H-units somehow covalently attached to it, preferably as end groups; a dendritic structure with the 4H-units attached to it as end groups, and/or in the dendritic arms; or a (multifunctional) branched or hyperbranched structure with the 4H-units attached to it as end groups, and/or in the branches. The (co)polymers may have any kind of microstructure, such as a random, a block, a segmented or a randomly segmented structure, with the 4H-units attached to this co-polymer in any fashion, such as end-capped, incorporated in the polymer chain or grafted from the backbone.

In a preferred embodiment of this invention, component (a) comprises a star shaped polymer that is (partly) end-functionalized with 4H-units, or component (a) comprises a linear polymer to which several 4H-units are grafted, or component (a) comprises a linear (co)polymer with the 4H-units attached to it as end groups and in the polymer backbone. The preferred ranges of the number of 4H-units are disclosed above.

More preferably, component (a) comprises a linear (co) polymer with the 4H-units attached to it as end groups and in the polymer backbone. Most preferably, component (a) comprises a linear (co)polymer with the 4H-units attached to it in the polymer backbone.

It is furthermore preferred to use components (a) with relative low number average molecular weights $M_n$, preferably in the range from 100 to 100000, more preferably from 100 to 60000, even more preferably 800 to 40000, most preferably from 2000 to 35000, in order to allow melt-processing of the supramolecular bioresorbable or biomedical material at temperatures preferably lower than 200° C., more preferably lower than 150° C., and most preferably lower than 100° C., or to process them from solutions at concentrations higher than 10% by weight, preferably higher than 15% by weight.

Optionally, ionic or ionogenic groups may be incorporated in component (a) in order to make the material more hydrophilic and thereby facilitating water-solubility or water swelling of the supramolecular bioresorbable or biomedical material (i.e. gelling). Preferred ionogenic groups are N-methyldiethanolamine, 2,6-bis-(hydroxymethyl)-pyridine and 2,2-bis(hydroxymethyl)-propionic acid.

In addition, component (a) may contain one or more hydrophilic polymeric blocks in its polymer chain in order to facilitate water-solubility or water swelling of the supramolecular bioresorbable or biomedical material (i.e. gelling). These hydrophilic polymeric blocks are preferably derived from polyethylene glycol polymers, preferably having a number average molecular weight $M_n$ from 200 to 50000, more preferably from 500 to 6000.

Component (a) can in particular be used to tune the mechanical properties of the supramolecular bioresorbable material of this invention. In a preferred embodiment of this invention, component (a) has an elongation at break of at least 140%. In another preferred embodiment of this invention component (a) has an E-modules >35 MPa.

Preferably, component (a) contains at least three 4H-units on average to counterbalance components (b) if component (b) has less than two 4H-units, the latter optionally acting as supramolecular chain stopper.

The 4H-Unit

It is preferred that in formulas (1) and (2) n equals 4 so and that the 4H-unit comprises four donors or acceptors in the arrays $X_1 \ldots X_4$ and $Y_1 \ldots Y_4$. The 4H-unit may be self-complementary (i.e. the two hydrogen bonded units have an equal array of donors and acceptors), or non self-complementary (i.e. the two hydrogen bonded units have two different arrays of donors and acceptors). Preferably, the 4H-unit comprises two successive donors, followed by two successive acceptors, i.e. it is preferred that $X_1$ and $X_2$ are donors and $X_3$ and $X_4$ are acceptors. Preferably, the donors and acceptors are O, S, and N atoms. The 4H unit is in detail disclosed in WO 98/14505 and in U.S. Pat. No. 6,320,018 which are expressly incorporated by reference.

According to a preferred embodiment of the present invention the 4H-unit has the general formula (3) or formula (4), and tautomers thereof:

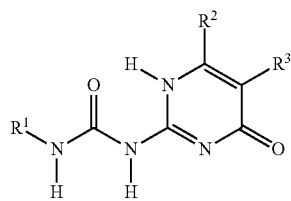

(3)

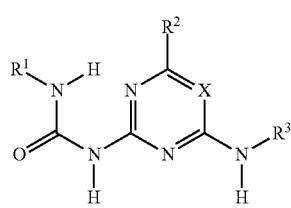

(4)

wherein X is a nitrogen atom or a carbon atom bearing a substituent $R^8$, preferably a nitrogen atom, and wherein $R^1$, $R^2$, $R^3$ and $R^8$ are independently selected from the group consisting of:
(a) hydrogen;
(b) $C_1$-$C_{20}$ alkyl;
(c) $C_6$-$C_{12}$ aryl;
(d) $C_7$-$C_{12}$ alkaryl;
(e) $C_7$-$C_{12}$ alkylaryl;
(f) polyester groups having the formula (5)

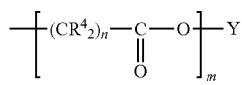

(5)

wherein $R^4$ and Y are independently selected from the group consisting of hydrogen and $C_1$-$C_6$ linear or branched alkyl, n is 1-6 and m is 10 to 100;
(g) $C_1$-$C_{10}$ alkyl groups substituted with 1-4 ureido groups according to the formula (6)

$R^5$—NH—C(O)—NH— (6)

wherein $R^5$ is selected from the group consisting of hydrogen and $C_1$-$C_6$ linear or branched alkyl;
(h) polyether groups having the formula (7)

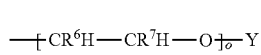

(7)

wherein $R^6$, $R^7$ and Y are independently selected from the group consisting of hydrogen and $C_1$-$C_6$ linear or branched alkyl and o is 10-100;
(i) oligopeptide groups consisting of sequences of 1 to 50, preferably 1 to 10, amino acids; and
wherein the 4H-unit is bonded to a polymer backbone via $R^1$, $R^2$ and/or $R^3$ (so that $R^1$, $R^2$ or $R^3$ represent a direct bond) with the other R groups representing, independently a side chain according to (a)-(h).
According to the invention, $R^1$, $R^2$, $R^3$ and $R^8$ are preferably independently selected from the group consisting of groups (a)-(h) disclosed above.

In a first preferred embodiment, the 4H-unit is bonded to a polymer backbone via $R^1$ (so that $R^1$ constitutes a direct bond), while $R^2$ and $R^3$ are independently any one of the groups (a)-(i) defined above, preferably group (b), more preferably 2-ethylpentyl or methyl and most preferably methyl. Most preferably, the 4H-unit is bonded to the polymer backbone via $R^1$, whereas $R^2$ is any one of the groups (a)-(h) defined above, more preferably group (b), even more preferably 2-ethylpentyl or methyl and most preferably methyl, and $R^3$ is hydrogen.

In a second preferred embodiment, the 4H-unit is bonded to a polymer backbone via $R^1$ and $R^2$ (so that $R^1$ and $R^2$ constitute direct bonds), while $R^3$ is any one of the groups (a)-(i) defined above, preferably group (a) or (b), more preferably group (a).

In a third preferred embodiment, the 4H-unit is bonded to a polymer backbone via $R^1$ and $R^3$ (so that $R^1$ and $R^3$ constitute a direct bond), while $R^2$ is any one of the groups (a)-(i) defined above, preferably group (b), more preferably 2-ethylpentyl or methyl and most preferably methyl. This third preferred embodiment if more preferred than the first and second preferred embodiments.

As will be apparent to the person skilled in the art, the groups (b)-(i) defined above may be linear, branched or cyclic where appropriate.

Component (b)

Additionally, the supramolecular bioresorbable or biomedical material of the present invention comprises a biologically active compound as a component (b). Preferably, the component (b) is selected from the group consisting of biologically active compounds with at least one 4H-unit up to a maximum of ten 4H-units, preferably one to four, and most preferably two to four 4H-units. These 4H-units are covalently attached to the biologically active compound.

If no component (c) is present (vide infra), then the amount of component (b) is 0.01 to 50.00 percent by weight and the amount of component (a) is 50.00-99.99 percent by weight, based on the total weight of the supramolecular bioresorbable or biomedical material, as is disclosed above. According to this embodiment, it is preferred that the weight range of component (a) is 70.00-99.99 percent by weight, and even more preferably 90.00-99.95 percent by weight, whereas the preferred weight range for component (b) is 0.01-30 percent by weight, and even more preferably 0.05-10.00 percent by weight. All these weight ranges are based on the total weight of the supramolecular bioresorbable or biomedical material. Moreover, component (b) may comprise one or more different biologically active compounds.

The biologically active compound can be any compound that displays bioactivity as disclosed above. A 'biologically active compound', as used herein, includes a compound that is biomedically relevant. It further provides a therapeutic, diagnostic, cosmetic, medicinal or prophylactic effect, a compound that effects or participates in tissue growth, cell growth, cell differentiation, cell signalling, cell homing, protein absorption, i.e. a compound that may be able to invoke a biological action, or could play any other role in one or more biological processes. Such compounds include, but are not limited to, antimicrobial agents (including antibacterial and anti-fungal agents), anti-viral agents, anti-tumor agents, anti-thrombogenic agents, anti-coagulant agents, lubricating agents, imaging agents, drugs, medicines, hormones, immunogenic agents, growth factors, cytokines, chemokines, (fluorescent) dyes, contrast agents, nucleic acids such as for example single or double stranded DNA and single or double stranded RNA, lipids, lipopolysaccharides, (poly)saccharides, vitamins, and peptides, polypeptides and proteins in general, biotinylated compounds or other compound that target biologically relevant molecules.

A non-limiting, preferred and important group of species that can be used as component (b) according to the present invention is formed by peptides, polysaccharides and proteins. Peptides include di-, tri- and tetrapeptides as well as oligopeptides and polypeptides as is known to the person skilled in the art.

In a preferred embodiment, component (b) comprises a growth factor, an anti-microbial agent, a thrombin inhibitor, or an anti-thrombogenic agent. A growth factor is defined as a protein or peptide that has a beneficial effect on the growth, proliferation and/or differentiation of living cells. According to a more preferred embodiment of this invention, the supramolecular bioabsorbable material is advantageously used as a scaffold for tissue engineering, wherein the growth factor is non-covalently bound to a polymer.

Examples of preferred growth factors are Bone Morphogenetic Proteins (BMP), epidermal growth factors, e.g. Epidermal Growth Factor (EGF), fibroblast growth factors, e.g. basic Fibroblast Growth Factor (bFGF), Nerve Growth Factor (NGF), Bone Derived Growth Factor (BDGF), transforming growth factors, e.g. Transforming Growth Factor-.beta.1 (TGF-.beta.1), and human Growth Hormone (hGH).

If the supramolecular material is a supramolecular biomedical material, it is according to another preferred embodiment used as a biomedical coating composition, wherein the anti-thrombogenic agent is non-covalently bound to a polymer. Non-limiting examples of preferred anti-thrombogenic agents are heparin, heparin analogues, heparin complexes, and molecules comprising a sulfonated glycosaminoglycan moiety. The anti-thrombogenic agent may also be a heparin covalently bonded to one or more polymers as disclosed in WO 02/34312, incorporated by reference herein. A preferred class of anti-thrombogenic agents consists of heparin, heparin analogues, heparin complexes, molecules comprising a sulfonated glycosaminoglycan moiety, and heparinised polymers as disclosed in WO 02/34312.

Further examples of peptides or proteins which may advantageously be included in the supramolecular bioresorbable or biomedical material include immunogenic peptides or immunogenic proteins, e.g. toxins, viral surface antigens or parts of viruses, bacterial surface antigens or parts of bacteria, surface antigens of parasites causing disease or portions of parasites, immunoglobulins, anititoxins, antigens.

Although, in view of the thermal instability of peptides, polysaccharides and proteins, the method according to the present invention is particularly useful for preparing materials loaded with peptides, polysaccharides and proteins, it is obviously also possible to load the supramolecular bioresorbable or biomedical material with a substance other than a peptide, a polysaccharide or a protein. Such biologically active agents which may be incorporated include non-peptide, non-polysaccharide and non-protein drugs and inorganic compounds. It is possible within the scope of the present invention to incorporate drugs of a polymeric nature, but also to incorporate drugs or vitamins of a relatively small molecular weight of less than 1500, or even less than 500.

Examples of non-peptide, non-polysaccharide or non-protein drugs which may be incorporated include the following: anti-tumor agents, antimicrobial agents such as antibiotics or hemotherapeutic agents, antifungal agents, antiviral agents, anti-inflammatory agents, anti-gout agents, centrally acting analgesics, local anesthetics, centrally active muscle relaxants, hormones and hormone antagonistics, corticosteroids such as mineralocorticosteroids or glucocorticosteroids, androgents, estrogens, progestins.

Examples of inorganic compounds, which may be incorporated, include, but are not limited to reactive oxygen scavengers or bone-extracts like apatite or hydroxyapatite.

Component (b) can be used as such, or can be chemically modified with one or more 4H-units. This chemical modification can be done by regular organic synthesis procedures, e.g. as coupling methods using succinimide esters, sulfhydryl reactive agents, azides, (thio)isocyanates, carbiodiimides, aldehydes, or Cu(I)-catalyzed Huisgen [2+3] dipolar cycloadditions, or by regular solid state synthesis procedures which are known to the person skilled in the art. Moreover, in case of peptides and proteins, this chemical modification can be done using native chemical ligation with a peptide or protein containing a C-terminal thio-ester and a 4H-unit with a N-terminal cysteine, native chemical ligation is known to people skilled in the art.

Optionally, the 4H-unit can be bonded to component (b) via a (bio)degradable linker that can be cleaved in vivo. In such a way the native component (b) is gradually released from the material, for example to induce an enhanced therapeutic effect. Non-limiting examples of cleavable linkers are esters or oligopeptides that are cleaved by enzymatic activity, such as the cleavage of the peptide Gly-Phe-Leu-Gly by cysteineproteases.

Additionally, two or more different components (b) may be present in the supramolecular bioresorbable or biomedical material. This is especially beneficial when the bioactivity is based on multivalent and/or synergistic interactions. A non-limiting example of such interaction is the cell adhesion advantageously mediated by a combination of RGD and PHSRN peptides.

Component (c)

The supramolecular bioresorbable or biomedical material according to the present invention preferably also comprises a third component (c), said third component (c) being a bioresorbable polymer.

Preferably, this bioresorbable polymer comprises one up to a maximum of fifty 4H-units, preferably one to thirty, more preferably two to twenty, and most preferably four to twenty. These 4H-units are covalently attached to the polymer chain. The supramolecular bioresorbable or biomedical material of this invention can obviously comprise different types of components (c), wherein these components are for example of different chemical nature and/or of different molecular weight, and can contain different numbers of 4H-units. It is obviously also possible that these polymers are constituted from elements of different chemical nature and/or of different molecular weight.

Component (c) may be any bioresorbable polymer. However, it is preferred that component (c) is selected from the group consisting of polyethers (preferably aliphatic), aliphatic polyesters, aromatic polyesters, polyamides (preferably aliphatic; for example polypeptides), polycarbonates (preferably aliphatic), polyorthoesters, polysaccharides, polyvinylalcohols (preferably partly esterified). It is even more preferred that component (c) is selected from the group consisting of aliphatic polyethers, aliphatic polyesters, aliphatic polyamides, aliphatic polycarbonates, aliphatic polyorthoesters, polysaccharides and partially esterified polyvinylalcohols. In another embodiment of this invention, component (c) contains any combination of polymer types, for example combinations of the preferred group of polymers disclosed above. According to a preferred embodiment of the invention, the polymer backbone is selected from the group consisting of polysaccharides, polyether and copolyethers based on, for example, ethyleneoxide, propyleneoxide, or tetrahydrofuran; polyesters and copolyesters made by polycondensation, based on, for example, adipic acid and diols such as glycols or hydroxyacids, such as lactic acid; polyesters and copolyesters made by ringopening polymerisation, based on, for example, ε-caprolactone, glycolide, lactide, δ-valerolactone, 1,4-dioxane-2-one, 1,5-dioxepan-2-one, oxepan-2,7-dione; polycarbonates and copolycarbonates based on, for example, 1,6-hexanediol polycarbonate; polycarbonates and copolycarbonates made by ringopening polymerization based on, for example, trimethylenecarbonate, 1,3-dioxepane-2-one, 1,3-dioxanone-2-one, 1,3,8,10-tetraoxacyclotetradecane-2,9-dione; or polyorthoesters, based on, for example, 3,9-diethylene-2,4,8,10-tetraoxaspiro[5.5]undecane; polymers and copolymers based on combinations of these preferred polymers. Also different combinations of these preferred polymers can be present in component (c).

The number average molecular weight $M_n$ of component (c) is preferably in the range from 100 to 100000, more preferably from 100 to 60000, even more preferably 800 to 40000, most preferably from 2000 to 35000 Dalton.

Component (c) can have all kinds of different architectures: a linear (co)polymer with the 4H-units attached to it as endgroups, and/or in the polymer backbone and/or grafted onto the polymer chain; a star shaped (co)polymer with the 4H-units somehow attached to it, preferably as endgroups; a dendritic structure with the 4H-units attached to it as endgroups, and/or in the dendritic arms; or a (multifunctional) branched or hyperbranched structure with the 4H-units attached to it as endgroups, and/or in the branches, preferably only as endgroups. The co-polymers can have any kind of microstructure, such as a random, a block, a segmented or a randomly segmented structure, with the 4H-units attached to this co-polymer in any fashion, such as end-capped, incorporated in the polymer chain or grafted from the backbone.

Preferably, component (c) comprises a star shaped polymer that is (partly) end-functionalized with 4H-units, a linear polymer to which several 4H-units are grafted, or a linear (co)polymer with the 4H-units attached to it as end groups and in the polymer backbone. More preferably, component (c) comprises a linear (co)polymer with the 4H-units attached to it as end groups and in the polymer backbone. Most preferably, component (c) comprises a linear (co)polymer with the 4H-units attached to it in the polymer backbone.

Like component (a), ionic or ionogenic groups may optionally be incorporated in component (c) in order to make the material more hydrophilic and thereby facilitating water-solubility or water swelling of the material (i.e. gelling). Preferred ionogenic groups are disclosed for component (a). In addition, component (c) may contain one or more hydrophilic polymeric blocks in its polymer chain in order to facilitate water-solubility or water swelling of the material (i.e. gelling). These hydrophilic polymeric blocks are preferably derived from polyethylene glycol polymers, preferably having a number average molecular weight $M_n$ from 200 to 50000, and more preferably from 500 to 6000.

Method of Preparing the Supramolecular Bioresorbable or Biomedical Material

The present invention also provides a method of preparing the supramolecular bioresorbable or biomedical material. This method comprises blending component (a), which predominantly attributes to the mechanical strength of the supramolecular bioresorbable or biomedical material, and component (b) which predominantly attributes to the biological activity of the supramolecular bioresorbable or biomedical material. According to a preferred embodiment of the present invention, this method comprises blending component (a), component (b) and component (c), the latter predominantly modifying and/or attributing to the bioresorption of the supramolecular bioresorbable or biomedical material. The blending of components (a), (b) and (c) results in supramolecular bioresorbable or biomedical materials with the desired material properties. In particular, if all components comprise 4H-units, they will all strongly contribute to strong physical interactions between the different components in the blend. In particular, it is therefore preferred according to the present invention that all three components (a)-(c) have at least one 4H-unit. The blending of all components can be done by conventional processes, i.e. solution processing or melt-processing, or a combination of both.

The concept of supramolecular blending of the different components also allows tuning the biodegradation behaviour of the supramolecular bioresorbable or biomedical materials, as this behaviour is determined by the degradation behaviour of all the added components.

Preparation and Processing of the Supramolecular Bioresorbable or Biomedical Material According to the supramolecular modular approach, the supramolecular bioresorbable or biomedical material can be obtained in three different ways: method (i) comprises blending the different components (a), (b) and optionally (c) with each other in conjunction with a medium consisting of one or more solvents, in which these components are dissolved or dispersed, preferably dissolved. This first method (i) is preferably followed by processes for dissolved polymers known in the art.

A second method (ii) comprises blending the different components (a), (b) and optionally (c) with each other in the bulk at elevated temperatures, preferably 40° to 150° C. (vide infra). This second method (ii) is preferably followed by solventless processes for polymers known in the art.

A third method (iii) comprises a combination of methods (i) and (ii). Hence, method (iii) comprises for example first blending component (b) with component (c) according to method (i), followed by blending component (a) and the blend of components (b) and (c) according to method (ii). Alternatively, method (iii) comprises first blending component (a) with component (b) according to method (i), followed by blending component (c) and the blend of components (a) and (b) according to method (ii). The other alternatives will be apparent to the person skilled in the art.

According to an especially preferred embodiment of the invention, methods (i) and (ii) comprises the in situ preparation of components (a) and/or (c).

Processing according to method (i) can be done from organic solvents or aqueous media, depending on the solubility of different components. Preferably, a solvent or mixture of solvents is used that is acceptable for biomedical uses, such as water, acetone, methyl ethyl ketone, THF, DMSO, NMP, supercritical $CO_2$ or aliphatic alcohols, such as ethanol. The supramolecular bioresorbable or biomedical material is preferably obtained by solvent casting, dip-coating, freeze-drying, precipitation casting, spray coating, painting, roll-coating, foaming, solvent spinning, wet spinning, electro-spinning, micro-contact printing, ink jet printing, particulate-leaching techniques, phase-separation techniques or emulsion processes.

If the supramolecular material is a biomedical coating composition, the choice of solvent(s) should be such that the desired viscosity of the solution for the coating process is obtained, preferably polar solvents should be used to reduce hydrogen bonding between the polymers. Moreover, the solvent has preferably a low boiling point in order to facilitate removal from the solvent(s) after the coating process, and the solvent (or solvent mixture) has preferably only limited toxicity. Therefore, drying of the supramolecular material is required after the coating process and is preferably followed by extensive washings with water or water containing a pH-buffer.

As will be known by persons skilled in the art, special care needs to be taken to clean the substrate surface when the supramolecular material is applied as a coating to this substrate. For example, wettability of the substrate can be improved by liquid etching techniques, such as the use of chromic acid, aqueous sodium hydroxide and fuming sulfuric acid, or plasma etching techniques.

Processing according to method (ii) is done at temperatures sufficient high to allow processing of the components although temperatures should be not too high to prevent degradation of the different components, especially component (b). Preferably, processing temperatures are in between 40° C. and 150° C., most preferably in between 50° C. and 120° C. The supramolecular bioresorbable or biomedical materials are preferably obtained by extrusion, reactive-extrusion, micro-extrusion, fused deposition modeling, moulding, lamination, film-blowing, reaction injection molding (RIM), spinning techniques, rapid prototyping. or by thermal or photo-curing of a coating.

The amount of component (a) in the supramolecular bioresorbable or biomedical material is preferably 50.00-99.99 percent by weight if no component (c) is present. According to this embodiment, component (a) is more preferably present between 70.00-99.99 percent by weight, and most preferably between 90.00-90.95 percent by weight The amount of component (b) in the supramolecular bioresorbable or biomedical material is preferably 0.01-50.00 percent by weight if no component (c) is present. According to this embodiment, component (b) is more preferably present between 0.01-30.00 percent by weight, and most preferably between 0.05-10.00 percent by weight.

If component (c) is present in the supramolecular bioresorbable or biomedical material according to the invention, the weight ratios of components (a)-(c) are preferably as follows: 20-59.99 percent by weight of (a), 0.01-40.00 percent by weight of (b), and 0.01-40.00 percent by weight of (c). More preferably, the weight ratios of components (a)-(c) are 40.00-69.99 percent by weight of (a), 0.01-30.00 percent by weight of (b), and 0.01-30.00 percent by weight of (c). All percentages by weight enlisted here for the supramolecular bioresorbable or biomedical material are based on the total weight of the supramolecular bioresorbable or biomedical material.

Highly porous structures can be obtained from the supramolecular bioresorbable materials of this invention by techniques known in the art, such as freeze-drying, particulate leaching, e.g. by using salts or sugars, and electro-spinning Highly porous (interconnecting) structures or non-woven fabrics are beneficial towards cell-attachment or proliferation, and allow the growth of tissue inside the scaffold. These structures can, for example, be used as porous scaffolds used in tissue-engineering, as prosthesis or implants.

Optionally, the supramolecular bioresorbable or biomedical material can be used to prepare a hydrogel, i.e. a gel in which the liquid is water. Hydrogels can be obtained by persons skilled in the art by balancing the ratio of hydrophilic and hydrophobic components in components (a) and optionally (c) in the formulation. Hydrogel materials have a high water content, potentially mimicking different roles of the extracellular matrices in tissue. Consequently, hydrogels find many uses in biomedical applications such as controlled drug delivery, delivery matrices or as coatings.

According to this invention, additional ingredients other than (a), (b), or optionally (c), may be added to the material such as excipients known in the art such as for example anti-oxidants and pH-buffers.

Applications

The supramolecular bioresorbable or biomedical materials according to the invention are preferably suitable for applications related to biomedical applications. In particular, the supramolecular bioresorbable materials are not only useful for controlled release of drugs or medical imaging technologies (for example MRI), but also for cosmetic applications and in agricultural applications, such as in herbicides and pest control.

On the other hand, the biomedical materials are in particular suitable as materials for tissue-engineering, materials for the manufacture of a prosthesis or an implant. More preferably, the supramolecular biomedical materials are useful for biomedical coatings with controlled release of drugs, biomedical coatings that have anti-thrombogenic or anti-microbial activity, biomedical coatings that have enhanced lubrication. The biomedical coating can be applied on prothesis, implants, stents, catheters, or other medical devices that come in contact with living tissue. According to another more preferred application, the supramolecular biomedical material is useful as filling material for cosmetic and in reconstructive plastic surgery.

EXAMPLES

The following non-limiting examples further illustrate the preferred embodiments of the invention. When not specifically mentioned, chemicals are obtained from Aldrich.

Example 1

Preparation of UPy1

1,6-Hexyldiisocyanate (650 g) and methylisocytosine (or 2-amino-4-hydroxy-6-methyl-pyrimidine, 65.1 g) were suspended in a 2-liter flask. The mixture was stirred overnight at 100° C. under an argon atmosphere. After cooling to room temperature, a liter of pentane was added to the suspension, while stirring was continued. The product was filtered, washed with several portions of pentane and dried in vacuum. A white powder was obtained. $^1$H NMR (400 MHz, CDCl$_3$): δ 13.1 (1H), 11.8 (1H), 10.1 (1H), 5.8 (1H), 3.3 (4H), 2.1 (3H), 1.6 (4H), 1.4 (4H). FT-IR (neat): ν (cm$^{-1}$) 2935, 2281, 1698, 1668, 1582, 1524, 1256.

Example 2

Preparation of UPy2

2-Amino-4-hydroxy-5-(2-hydroxy ethyl)-6-methyl-pyrimidine (12 gram) was suspended in IPDI (150 mL) and was stirred overnight at 90° C. under an argon atmosphere. A clear solution developed. The solution was cooled and precipitated in hexane. The solid was filtered, stirred in another portion of hexane, and then the product was isolated by filtration, washing with hexane and drying of the residue. Yield: 98%. $^1$H NMR (400 MHz, CDCl$_3$): δ 13.1 (1H), 11.9 (1H), 10.2 (1H), 4.8-4.5 (1H), 4.2 (2H), 4.0-3.2 (3H), 3.1-2.9 (3H), 2.7 (2H), 2.3 (3H), 1.9-1.6 (4H), 1.4-0.8 (26H). FT-IR (neat): ν (cm$^{-1}$) 2954, 2254, 1690, 1664, 1637, 1590, 1532, 1461, 1364, 1307, 1257, 1034, 791. MALDI-TOF-MS, [M$^+$]=614, [M+Na$^+$]32 636.

Example 3

Preparation of UPy3

A mixture of methylisocytosine (10 g) and carbodiimidazole (20.7 g) in dried DMSO (50 mL) was heated and stirred at 100° C. under an argon atmosphere for 2 hours. The resulting solid was filtered and washed with dry acetone until a white powder remained in the filter that subsequently was dried in vacuo and stored over $P_2O_5$. FT-IR (neat): ν $(cm^{-1})$ 3174, 1701, 1644, 1600, 1479, 1375, 1320, 1276.

Example 4

Preparation of UPy4

6-(2-Ethylpentyl) isocytosine (0.42 g) was dissolved in 5 mL chloroform. To this clear solution 1,1-carbonyldiimidazole (CDI) (0.71 g) was added. The reaction mixture was stirred for 3 hours at room temperature. The entire mixture was extracted three times with brine. The water layers were combined and extracted with chloroform. The combined chloroform layers were dried with $Na_2SO_4$ and filtrated. The remaining organic layer was dried under reduced pressure resulting in a light yellow powder in a yield of 66%. $^1H$ NMR (400 MHz, $CDCl_3$): δ 8.8 (1H), 7.6 (1H), 7.1 (1H), 5.8 (1H), 2.5 (1H), 1.7 (4H), 1.3 (4H), 1.0 (3H), 0.9 (3H).

Example 5

Preparation of UPy5

UPy3 (0.9 g) and 1,6-diaminohexane (0.54 g; 1.1 eq.) were stirred for 72 hours at room temperature in 15 mL of THF. The mixture was kept under argon. Ethanol (25 mL) was added, and the suspension was stirred for half an hour. The solid was filtered, washed with several 10 mL portions of ethanol and dried. Resulting in 0.86 g of 2(6-aminohexylaminocarbonylamino)-6-methyl-4[1H]pyrimidinone. $^1H$ NMR (400 MHz, $D_2O$ with a drop of $CH_3COOH$): δ=5.9 (1H), 3.2 (2H), 2.9 (2H), 2.2 (3H), 1.7-1.2 (8H).

Example 6

Preparation of UPy6

Methylisocytosine (5.2 gram) was added to isophoronediisocyanate (IPDI, 50 mL) and subsequently stirred at 90° C. under an argon atmosphere for 3 days. The resulting clear solution was precipitated in heptane. The white gom was collected, heated in 150 mL heptane, cooled on ice and filtered. The same procedure was repeated once more with the white residue, resulting in a white powder consisting of ureidopyrimidinone with one IPDI unit. This product (10.22 g) was dissolved in chloroform (20 mL), and thereafter hydroxy ethyl acrylate (HEA, 3.6 mL) and 1 drop of dibutyl tin dilaurate (DBTDL) were added. The mixture was stirred at an oil bath temperature of 65° C. for 4 hours, and was then cooled and filtered. The filtrate was concentrated and dropped into an excess of diethylether. The precipitate was collected by filtration, and was washed with diethylether. Drying in vacuo gave a solid product. $^1H$ NMR (400 MHz, $CDCl_3$): δ 13.1 (1H), 11.7-12.0 (1H), 9.8-10.0 (1H), 6.4 (1H), 6.2 (1H), 5.8 (2H), 5.2 (1H), 4.3 (4H), 4.1-3.6 (1H), 3.1-2.9 (2H), 2.1 (3H), 2.0 (3H), 1.8-1.5 (2H), 1.4-0.8 (13H) 1.9 (3H), 1.7-1.2 (8H). FT-IR (neat): ν 3212, 2954, 1697, 1660, 1572, 1520, 1242, 1165.

Example 7

Polymer I with 4H-Units

Telechelic hydroxy terminated PEO-6000 (10.20 g) was heated in vacuo in a 3-neck flask to 120° C. for 120 minutes and subsequently cooled down to 80° C. UPy2 (1.25 g) and two drops of dibutyltindilaurate dissolved in toluene (40 mL) were added to the polymer melt and the solution was stirred overnight under argon at 80° C. The reaction mixture was diluted with 40 mL THF and precipitated into diethylether. The material is white (semi-crystalline), elastic and tough. $^1H$ NMR (300 MHz, $CDCl_3/CD_3OD$): δ 4.1, 3.6, 2.8, 2.2, 1.8-1.4, 1.2-0.8.

Example 8

Polymer II with 4H-Units

Telechelic hydroxy terminated polycaprolacton with a molecular weight of 1250 D (25.9 g, dried in vacuo), UPy2 (10.9 g) and two drops of dibutyltindilaurate were dissolved in dry ethylacetate (130 mL) and stirred overnight at an oil bath temperature of 70° C. The next day, ethylacetate (70 mL) and ethanol (50 mL) were added to the reaction mixture, which was subsequently precipitated into ethanol. The polymer was isolated after drying of the precipitate, resulting in an elastic material. $^1H$ NMR (300 MHz, $CDCl_3$): δ 13.1, 12.0, 10.1, 4.5-3.8, 3.0, 2.6-2.2, 2.0-0.8. SEC (THF, PS-standards): $M_n$=8.8 kD, D=2.

Example 9

Polymer III with 4H-Units

Telechelic hydroxy terminated PEO-3000 (12.78 g) was heated in vacuo in a 3-neck flask to 120° C. for 30 minutes, followed by the addition of 5 drops dibutyltindilaurate and UPy1 (2.51 g). This heterogeneous reaction mixture was subsequently stirred with a mechanical stirrer under an argon atmosphere and heated to 140° C. After 10 minutes stirring at 140° C. a clear homogeneous viscous liquid was obtained that after cooling was isolated as a hard brittle white material. $^1H$ NMR (400 MHz, $CDCl_3$): δ 13.1, 11.9, 10.1, 5.8, 5.0, 4.2, 3.8-3.3, 3.2, 3.1, 2.1, 1.6-1.2. FT-IR (neat): ν $(cm^{-1})$ 2882, 1698, 1663, 1588, 1527, 1466, 1342, 1100, 962, 841. SEC (THF, PS-standards): $M_n$=2.9 kD, D=1.2

Example 10

Polymer IV with 4H-Units

Bis(aminopropyl) endblocked polysiloxane DMS A21 with a viscosity of 100-120 cSt was obtained from Gelest. UPy3 (1.5 g) was added to a solution of DMS A21 (14.7 g) in tetrahydrofuran (200 mL). This mixture was subsequently heated to an oil bath temperature of 80° C. and stirred at this temperature for 16 h under an argon atmosphere. Chloroform (200 mL) was added to the reaction mixture that was subsequently filtered over silica. The clear filtrate was washed twice with saturated sodium chloride solution in water. The organic fraction was dried over $Na_2SO_4$, filtered and dried in vacuo to obtain an off-white, clear, elastic material. Molecular mass (Mn) is 5.0 kg/mol; molecular weight distribution 1.8, determined by gel permeation chromatography (polystyrene standards). $^1H$ NMR (400 MHz, $CDCl_3$): δ 13.1, 11.9, 10.2, 5.9, 3.3, 2.3, 1.6, 0.6, 0.4--0.1. FT-IR (neat): ν (cm$^{-1}$) 2961, 1698, 1659, 1587, 1527, 1258, 1010, 780. SEC (THF, PS-standards): $M_w$=8.1 kD.

Example 11

Polymer V with 4H-Units

Kraton L-2203, produced by Kraton Polymers, (average molecular weight $M_n$, =3400, 10 g) was dissolved in dry toluene (100 mL). To this mixture was added UPy1 (1.75 g) and 2 drops of dibutyltindilaurate, subsequently the turbid mixture was stirred at 80° C. under an argon atmosphere for 12 h. A sample was taken and checked for complete reaction with $^1$H NMR (disappearance multiplet at 3.6 ppm). The viscous reaction mixture was cooled to 70° C. while stirring and 0.3 mL of water was added. The reaction mixture was stirred for an additional hour, followed by precipitation in methanol (viscosity of reaction mixture can be lowered by the addition of more ethanol). The white gum was collected and dried in vacuo to obtain a slightly yellowish transparent rubber. Yield: 94%; $^1$H NMR (CDCl$_3$): δ 13.1, 11.9, 10.1, 5.8, 4.9, 4.6, 4.1, 3.8, 3.3, 3.2, 2.2, 1.6-1.1, 0.8.

Example 12

Polymer VI with 4H-Units

Telechelic poly(2-methyl-1,3-propylene adipate) (average molecular weight $M_n$=2.0 kD, hydroxy end groups, 5.55 g) was stripped three times with toluene and dissolved in toluene (25 mL) together with UPy2 (1.31 g) and few drops dibutyltindilaurate. The mixture was heated to 80° C. and stirred for 16 hours under an argon atmosphere. Subsequently it was verified with FT-IR whether the isocyanate-functions had disappeared, and the polymer was isolated by precipitation from a chloroform/methanol solution into ether and drying of the solid. $^1$H NMR (300 MHz, CDCl$_3$): δ 13.1, 12.0-11.8, 10.1-9.8, 5.0-4.6, 4.3-3.8, 3.4-2.8, 2.5-2.0, 1.9-1.6, 1.4-0.8. SEC (THF, PS-standards): $M_n$=15.5 kD, D=1.7.

Example 13

Polymer VII with 4H-Units

A mixture of telechelic hydroxy terminated poly(2-methyl-1,3-propylene adipate) with an average molecular weight of 2.0 kD (2.39 g) and telechelic hydroxy terminated polycaprolactone with an average molecular weight of 2.0 kD (2.39 g), was stripped three times with toluene and dissolved in chloroform (25 mL) together with monomer UPy2 (1.18 g) and few drops dibutyltindilaurate. The mixture stirred overnight at 60° C., followed by confirming the absence of isocyanate functions with FT-IR spectroscopy, UPy3 (0.35 g) was added and the solution diluted with 20 mL chloroform and put to reflux for another night. Again, it was verified with FT-IR whether the isocyanate-functions had disappeared, and the polymer was isolated by precipitation from a chloroform/ethanol solution into hexane and drying of the solid. $^1$H NMR (300 MHz, CDCl$_3$): δ 13.2-12.8, 12.1-11.8, 10.2-9.8, 5.8, 5.2-4.5, 4.4-3.6, 3.4-2.6, 2.6-2.0, 2.0-0.6. SEC (THF, PS-standards): $M_n$=12.2 kD, D=2.0.

Example 14

Polymer VIII with 4H-Units

Hydroxy-terminated polycaprolactone diol ($M_n$=2.1 kg/mole; obtained via ring-opening polymerization initiated by diethylene glycol; purchased from Acros) was dissolved in toluene, after which the toluene was removed under reduced pressure to co-evaporate the water. This procedure was repeated twice. This prepolymer (25.0 g; 12.5 mmol) was dissolved in dry chloroform (750 mL) after which UPy1 (8.8 g) was added. After addition of two drops of dibutyltindilaurate the solution was refluxed for 16 hours. The completeness of the reaction was checked with $^1$H and $^{13}$C NMR for the presence of OH end-groups. Then 5 gram silica kieselgel 60 and two drops of dibutyltindilaurate were added and the mixture was refluxed for 16 hours. With IR the absence of UPy1 in the solution was checked. After dilution of the mixture with chloroform, the silica was removed by filtration using hyflo. The solution was concentrated under reduced pressure. The material was precipitated from chloroform (500 mL) in hexane (4.0 L) and filtrated. The resulting material was dried for 24 hours in vacuo resulting in 24.4 g of 4H-unit containing telechelic polycaprolactone as a white fluffy material. $^1$H NMR (CDCl$_3$): δ 13.1, 11.9, 10.1, 5.9, 4.9, 4.2, 4.1, 3.7, 3.2, 2.3, 2.2, 1.6, 1.5, 1.4. FT-IR: ν=2941, 2865, 1729, 1699, 1669, 1587, 1527, 1461, 1418, 1359, 1251, 1162, 1105 cm$^{-1}$.

Example 15

Polymer IX with 4H-Units

Telechelic hydroxy terminated polycaprolactone with an average molecular weight of 1250 Dalton (10.94 g) was heated in vacuo in a 3-neck flask to 120° C. for 30 minutes, followed by the addition of 8 drops dibutyltindilaurate and UPy1 (5.13 g). This heterogeneous reaction mixture was subsequently stirred with a mechanical stirrer under an argon atmosphere and heated to 145° C. After 50 minutes stirring at 145° C. a homogeneous viscous paste was obtained that after cooling was isolated as a hard white material. IR-spectroscopy confirmed that the product did not contained isocyanates anymore. $^1$H NMR (400 MHz, CDCl$_3$): δ 13.2, 11.9, 10.2, 5.8, 4.9, 4.3, 4.1, 3.7, 3.4-3.1, 2.4-2.2, 3.1, 1.8-1.2. FT-IR (neat): ν (cm$^{-1}$) 2882, 1698, 1663, 1588, 1527, 1466, 1342, 1100, 962, 841. SEC (THF, PS-standards): $M_n$=2.1 kD, D=1.4

Example 16

Polymer X with 4H-Units

Telechelic hydroxy terminated polycaprolacton with a molecular weight of 2.0 kD (9.73 g), UPy2 (2.5 g) and a few drops of dibutyltindilaurate were dissolved in chloroform (100 mL) and stirred overnight at an oil bath temperature of 60° C. The next day the chloroform was evaporated, toluene (100 mL) and pyridine (20 mL) were added, as well as a second portion of UPy2 (0.5 g). The mixture was heated at an oil bath temperature of 120° C. for another night, and the polymer product was isolated by evaporation of the pyridine, precipitation from chloroform/methanol 10:1 into methanol and drying of the solid. Upon standing the material develops into a white (semi-crystalline), elastic polymer. $^1$H NMR (300 MHz, CDCl$_3$): δ 13.1, 12.0, 10.1, 4.5-3.8, 3.0, 2.6-2.2, 2.0-0.8. SEC (THF, PS-standards): $M_n$=38.5 kD, D=2.0.

Example 17

Polymer XI with 4H-units

Telechelic PEO-1500 (5.83 g) was stripped three times with toluene and was then dissolved in toluene (30 mL). UPy2

(2.39 g) in toluene (14 mL) was added as well as a few drops of dibutyltindilaurate and the solution was heated overnight under argon (oil bath temperature of 120° C.). The polymer was isolated by precipitation into diethylether. The material is white (semi-crystalline), elastic and tough. $^1$H NMR (300 MHz, CDCl$_3$/CD$_3$OD): δ 4.1, 3.6, 2.8, 2.2, 1.8-1.4, 1.2-0.8. SEC (THF, PS-standards): M$_w$=7.0 kD.

Examples of Bioactive Components (b)

Example 18

UPy-GRGDS

A GRGDS peptide was synthesized according to conventional solid phase peptide synthesis (SPPS) techniques using standard Fmoc-coupling chemistry on a Wang resin (the loading of the Wang resin with Fmoc-Ser(tBu)-OH was 0.63 mmole/g; Bachem). In all cases, the Fmoc-protection groups were deprotected with 20% piperidine in DMF. The protected (if necessary) amino acids (3 eq.; (Fmoc-Asp(OtBu)-OH, Fmoc-Gly-OH, Fmoc-Arg(Pmc)-OH and Fmoc-Gly-OH; Bachem) were dissolved in DMF. As coupling reagents 1-hydroxybenzotriazole (3.6 eq.) and diisopropylcarbodiimide (3.3 eq.) in DMF were used. The coupling of the 4H-unit to the free amine of the last amino acid (Gly) of the protected GRGDS peptide was performed on the solid support using UPy3 (5 eq.) in dry DMF (dried on molsieves) under an argon atmosphere for 16 hours at 50° C. This resulted in the protected UPy-GRGDS on the resin. The excess of UPy3 was washed away with acidic water. The peptide was deprotected and cleaved from the solid support with 95% trifluoro acetic acid (TFA) and 5% water. It was precipitated in (cold) diethylether, spun down and washed three times with diethylether. Subsequently, the peptide was freeze-dried three times from water with 10-20% acetonitrile which resulted in a white fluffy powder. UPy-GRGDS was purified using preparative reversed phase liquid chromatography (RPLC) if necessary. The compound was characterized with NMR techniques, IR, RPLC and mass spectrometry. $^1$H NMR (D$_2$O/ACN-d3): δ 5.98 (1H), 4.78 (1H), 4.48 (1H), 4.32 (1H), 3.98-3.84 (2H), 3.15 (2H), 2.90-2.78 (2H), 2.23 (3H), 1.85-1.61 (4H). The assignment of the $^1$H NMR spectrum is confirmed by 2D $^1$H,$^1$H-COSY spectroscopy. $^{19}$F NMR (D$_2$O/ACN-d3), with potassium hexafluoro phosphate as internal standard) showed that the sample contained less than 0.1 weight % TFA. FT-IR (neat): ν (cm$^{-1}$) 3280, 3182, 3073, 2948, 2542, 1701, 1642, 1528, 1413, 1224, 1180, 1135, 1076, 1046. RPLC-MS: one peak in chromatogram with m/z: Calcd. 641.3 g/mole. Obsd. [M+H]$^+$=642.2 g/mole and [M+H]$^{2+}$=321.7 g/mole.

Example 19

UPy-PHSRN

The PHSRN peptide was synthesized according to conventional solid phase peptide synthesis (SPPS) techniques using standard Fmoc-coupling chemistry on a Wang resin (the loading of the Wang resin with Fmoc-Asn(Trt)-OH was 0.43 mmole/g; Bachem). In all cases, the Fmoc-protection groups were deprotected with 20% piperidine in DMF. The protected (if necessary) amino acids (3 eq.; Fmoc-Arg(Pmc)-OH, Fmoc-Ser(tBu)-OH, Fmoc-His(Trt)-OH and Fmoc-Pro-OH for PHSRN); Bachem) were dissolved in DMF. As coupling reagents 1-hydroxybenzotriazole (3.6 eq.) and diisopropyl-carbodiimide (3.3 eq.) in DMF were used. The coupling of the 4H-unit to the free amine of the last amino acid (Pro) of the protected PHSRN peptide was performed on the solid support using UPy1 (8 eq.) in dry chloroform (molsieves) for 16 hours at 21° C. This resulted in the protected UPy-PHSRN on the resin. The excess of UPy1 was washed away with acidic water. The peptide was deprotected and cleaved from the solid support with 95% trifluoro acetic acid (TFA) and 5% water. It was precipitated in (cold) diethylether, spun down and washed three times with diethylether. Subsequently, the peptide was freeze-dried three times from water with 10-20% acetonitrile which resulted in a white fluffy powder. UPy-PHRSN was purified using preparative reversed phase liquid chromatography (RPLC) if necessary. $^1$H NMR (D$_2$O/ACN-d3): δ 8.58 (1H), 7.27 (1H), 5.92 (1H), 4.73 (1H), 4.66 (1H), 4.36 (1H), 4.15 (1H), 3.86 (2H), 3.40-3.05 (2H), 2.82-2.73 (2H), 2.21 (3H), 2.15 (1H), 2.03-2.00 (3H), 1.94-1.62 (4H), 1.54-1.46 (4H), 1.34-1.27 (8H). The assignment of the $^1$H NMR spectrum is confirmed by 2D $^1$H,$^1$H-COSY spectroscopy. $^{19}$F NMR (D$_2$O/ACN-d3), with potassium hexafluoro phosphate as internal standard) showed that the sample contained less than 1 weight % TFA. FT-IR (neat): ν (cm$^{-1}$) 3263, 2943, 1657, 1542, 1441, 1361, 1317, 1252, 1201, 1133, 1078. RPLC-MS: one peak in chromatogram with m/z: Calcd. 902.4 g/mole. Obsd. [M+H]$^+$=903.3 g/mole, [M+H]$^{2+}$=452.3 g/mole and [M+H]$^{3+}$=301.9 g/mole.

Example 20

UPy-Fluorescein

UPy4 (0.51 g) was added to a solution of hexanediamine (2.03 g) in chloroform at room temperature. The mixture was stirred overnight. Basic water (5 g NaOH in 20 mL water) was added to this mixture, and after centrifugation (5 min. at 4300 rpm) a clear water layer separated and was subsequently isolated. The basic water layer was brought to pH=6 with 3 M HCl in water. The amino-functional 4H-unit was isolated as a white precipitate was formed, which was extracted with chloroform. The chloroform layer was dried with Na$_2$SO$_4$ and evaporated. $^1$H NMR (CDCl$_3$): δ 13.25 (1H), 11.91 (1H), 10.21 (1H), 5.82 (1H), 3.27 (2H), 2.66 (2H), 2.31 (1H), 1.69-1.28 (16H), 0.90 (6H). FT-IR (neat): ν (cm$^{-1}$) 3064; 2956; 2856; 2927; 2856; 1939; 1664; 1594; 1558; 1520; 1428; 1265; 1178; 1117; 1073; 950; 840; 814; 773; 756; 728; 697. Elemental analysis: C, 61.34, H, 9.64; N, 19.82, calculated (C, 61.51, H, 9.46, N, 19.92). RPLC-MS: [M+H]$^+$=352.2 (calculated: 351.41); [isocytosine+H]$^+$=210.2 (calculated: 209.29); [UPy-C$_6$-UPy+H]$^+$=587.3 (calculated: 586.78) g/mole.

This amino-functional 4H-unit (123 mg) was added to fluorescein-isothiocyanate (132 mg) in a 2:1 mixture of methanol and chloroform and stirred at room temperature for 2 days. The solvents were removed under reduced pressure. The remaining orange precipitate was dissolved in 5 mL 0.2 M NaOH solution. Upon addition of 1.5 mL 1 M HCl solution a cloudy orange precipitate was formed. This was isolated by centrifugation. Subsequently, the yellow clear water layer was poured off. The product was purified using a Sephadex LH 20 column (1:1 dichloromethane: methanol). The product was dissolved in THF:water (1:1) and flushed over a small silica column. It was subsequently freeze-dried. $^1$H NMR (DMSO): δ 8.19 (1H), 7.91 (1H), 6.89 (1H), 6.81 (1H), 6.58 (4H), 6.46 (2H), 5.72 (1H), 3.51 (2H), 3.18 (2H), 2.18 (1H), 1.57-1.10 (16H), 0.74 (6H). LC-MS (direct injection): [M+H]$^+$=741.2 (calculated: 740.30); [2M+H]$^+$=1481.1;

[M$_{fragment}$+H]$^+$=210.2; [M$_{fragment}$+H]$^+$=352.3; [M$_{fragment}$+H]$^+$=390.3; [M$_{fragment}$+H]$^+$=707.3 g/mole.

Example 21

UPy-Biotin

To a solution of N-(+)-biotinyl-3-aminopropylammonium trifluoroacetate (165 mg, obtained from Sigma-Aldrich) in DMF (1.0 mL), Upy4 (124 mg) and diisopropyl-ethylamine (DIPEA; 133 mg) were added. The mixture was stirred at 60° C. for 7 hours. DMF was removed under reduced pressure and everything was dissolved in chloroform. The following extractions were performed; 3 times with brine and 3 times with 1 M HCl. The combined organic layers were dried with Na$_2$SO$_4$ and concentrated to 1.5 mL. This was precipitated in cold acetone and centrifugated. The acetone was poured off and the product was dried under reduced pressure at 40° C. for 2 hours. This resulted in a white powder in a yield of 65%. $^1$H NMR (400 MHz, CDCl$_3$): δ 13.32 (1H), 11.82 (1H), 10.07 (1H), 5.92 (1H), 4.51 (1H), 4.36 (1H), 3.37 (4H), 3.13 (1H), 2.90 (1H), 2.73 (1H), 2.39 (1H), 2.23 (2H), 1.81-1.19 (16H), 0.89 (6H). FT-IR (neat): ν (cm$^{-1}$) 3217; 3038; 2929; 2860; 1699; 1641; 1583; 1526; 1460; 1439; 1381; 1306; 1251; 1145; 1075; 1009; 951; 850; 796; 763; 739; 686. MALDI-TOF: 536.14 (calculated 535.71 g/mole), 301.07, 334.23 g/mole.

Example 22

UPy-Gd(III)-DTPA Complex

To a colourless solution of UPy4 (0.376 g, 1.24 mmol) in dichloromethane (5 mL) was slowly added a solution of t-butyl-6-amino-2-{{bis {2-[bis-(t-butoxycarbonylmethyl) amino]-ethyl}-amino}}hexanoate (0.713 g, compound obtained as described by: Anelli, P. L. et al. Bioconjugate Chem. 1999, 10, p. 137, compound 7). The solution was vigorously stirred for 12 h at 20° C. The yellowish solution was washed with 1M KHSO$_3$ (aq) pH 1.95 (2×10 mL). Subsequently, the organic layer was washed with 1 M K$_2$CO$_3$ (aq) pH 10 (3×10 mL) and brine (3×10 mL). The combined water layer was extracted with DCM (2×10 mL) and the organic layer was dried over MgSO$_4$. The reaction mixture was concentrated under reduced pressure, yielding a yellowish liquid (0.84 g). The crude product (0.730 g) was purified by column chromatography using EtOAc, yielding the protected SupraB-containing DTPA analogue in 0.51 g (R$_f$=0.5 (EtOAc)). $^1$H-NMR (CDCl$_3$): δ 13.3 (1H), 11.9 (1H), 10.2 (1H), 5.8 (1H), 3.5 (8H), 3.3-3.2 (3H), 3.0-2.6 (8H), 2.3 (1H), 2.0-1.2 (14H), 0.94 (6H). The assignment of the 1H-NMR spectrum was confirmed by 1H,1H-COSY. FT-IR (neat): ν (cm$^{-1}$) 2975, 2932, 1724, 1698, 1658, 1646, 1586, 1526, 1367, 1253, 1219, 1148. ESI-QTOF-MS: m/z [C$_{50}$H$_{89}$N$_7$O$_{12}$+H]$^+$ Calcd. 980.67 Da, Obsd. 980.71 Da; [C$_{50}$H$_{89}$N$_7$O$_{12}$+Na]$^+$ Calcd. 1002.65 Da, Obsd. 1002.65 Da.

This protected UPy-containing DTPA analogue was subsequently dissolved in dichloromethane (0.39 g) and TFA (2 mL) was added, followed by stirring the reaction mixture for 16 h at room temperature. After evaporation of the solvent a second portion of TFA (2 mL) and dry dichloromethane (5 mL) was added and stirring was continued overnight. The solution was concentrated in vacuo resulting in the TFA salt of the deprotected product which was additionally purified by dialysis at 60° C. (100 Da MWCO membrane) followed by freeze-drying, yielding the penta-acid as a white hygroscopic powder (0.266 g). $^1$H-NMR (D$_2$O, 348 K): δ6.2 (1H), 4.1 (8H), 3.6 (1H), 3.4 (4H), 3.3-3.1 (6H), 2.6 (1H), 2.0-1.2 (14H), 0.79 (6H). The assignment of the 1H-NMR spectrum was confirmed by 1H,1H-COSY. $^{19}$F-NMR spectroscopy confirmed the successful removal of TFA by the absence of a signal at −75.6 ppm. FT-IR (neat): ν (cm$^{-1}$) 3215, 2933, 2531, 1700, 1630, 1551, 1431, 1389, 1333, 1202. ESI-QTOF-MS: m/z [C$_{30}$H$_{49}$N$_7$O$_{12}$+H]$^+$ Calcd. 700.35 Da, Obsd. 700.40 Da; [C$_{30}$H$_{49}$N$_7$O$_{12}$+Na]$^+$ Calcd. 722.33 Da, Obsd. 722.40 Da.

The desired Gd(III) complex was prepared by adding a stoichiometric amount of GdCl3.6H$_2$O (4.97 mg) in demineralised water (3 mL) to a solution of the penta-acid (9.16 mg) in 0.3 m citrate buffer at pH 5.8. The buffered solution was vigorously stirred for 2 h at room temperature. The aqueous solution was extensively dialysed (100 Da MWCO membrane) and lyophilized. The resulting Gd(III) complex was obtained as a white hygroscopic powder (10.7 mg). FT-IR (neat): ν (cm$^{-1}$) 3384, 2932, 1696, 1579, 1407, 1183, 1135, 1083. ESI-MS: m/z [C30H46N7O12Gd+H]+ Calcd. 855.25 Da, Obsd. 855.27 Da; [C30H45N7O12NaGd+H]+ Calcd. 877.23 Da, Obsd. 877.27 Da. [C30H44N7O12Na2Gd+H]+ Calcd. 899.22 Da, Obsd. 899.27 Da. ICP-AES (Gd(III): Calcd. 50.0 μm, Obsd. 33.9 μm.

Example 23

UPy-Cysteine

A CGGKG peptide was synthesized according to conventional solid phase peptide synthesis (SPPS) techniques using standard Fmoc-coupling chemistry on a Wang resin (the loading of the Wang resin with Fmoc-Gly-OH was 0.75 mmole/g; Bachem). In all cases, the Fmoc-protection groups were deprotected with 20% piperidine in DMF. The protected (if necessary) amino acids (3 eq.; (Fmoc-Lys(Mtt)-OH, Fmoc-Gly-OH, Fmoc-Gly-OH and Fmoc-Cys(Trt)-OH; Bachem) were dissolved in DMF. As coupling reagents 1-hydroxybenzotriazole (3.6 eq.) and diisopropylcarbodiimide (3.3 eq.) in DMF were used.

The 4H-unit was coupled to the Lys on the resin when the Cys was still protected. The Lys was first selectively deprotected in a mixture of 90% DCM/5% TFA/5% triisopropylsilane for 15 minutes. The resin was washed for 2 times with DCM and for 4 times with DCM supplemented with 5% DIPEA. The coupling of the 4H-unit to the resulting free amine at the Lys was performed on the solid support using UPy1 (8 eq.) in dry chloroform (dried on molsieves) at a shaking table at 21° C. This resulted in the protected CGGK (UPy)G peptide on the resin. The excess of UPy1 was washed away with acidic water. The Fmoc-group on the Cys was removed with 20% piperidine in DMF. The peptide was deprotected and cleaved from the solid support with 95% trifluoro acetic acid (TFA), 2.5% water and 2.5% Tis. It was precipitated in (cold) diethylether, spun down and washed three times with diethylether. Subsequently, the peptide was freeze-dried three times from water with 10-20% acetonitrile which resulted in a white fluffy powder. The compound was characterized with $^1$H NMR and mass spectrometry. RPLC-MS: one peak in chromatogram with m/z: Calcd. 713.8 g/mole. Obsd. [M+H]$^+$=714.3 g/mole and an impurity of [M+H]$^+$=820.3 g/mole and [M+H]$^{2+}$=410.8 g/mole. $^1$H NMR (400 MHz, D$_2$O/ACN-d3): δ 6.34 (1H), 4.79 (1H), 4.74 (1H), 4.41 (2H), 4.32 (4H), 3.60 (2H), 3.44 (6H), 2.62 (3H), 2.31-2.04 (2H), 1.92-1.84-1.72 (12H).

Example 24

UPy-Heparine

Heparin sodium salt (1.0 g, Mn=12000, activity=195 IU/mg, Porcine Intestinal Mucosa, obtained from Merck Biosciences, Germany) was dissolved in water and passed through a Dowex 50X8 (H+) column, followed by dialyzing (MW cut-off=12000-14000) against water and lyophilization to obtain heparin (0.95 g). The carboxylic acid groups of heparin were activated by adding N-(3-dimethylaminopropyl)-N'-ethylcarbodiimide (EDC) and N-hydroxysuccinimide (NHS) to 2% solution by weight of lyophilized heparin in 0.05 M buffer of 2-morpholinoethane sulfonic acid (MES-buffer, pH=5.60), at a molar ratio of NHS:EDC:heparin-$CO_2H$ of 0.24:0.40:1.0. After 10 minutes pre-activation, UPy5 (64 mg) was dissolved in MES-buffer (3 mL, pH=5.60) and added to the NHS/EDC activated heparin solution (25 mL), resulting in a molar ratio of 6 to 1 (UPy5 to heparin). After 3 h the reaction mixture was dialyzed once against MES-buffer (pH=5.60), followed by extensive dialysis against water, followed by lyophilization to obtain heparin functionalized with approximately six 4H-units.

Example 25

UPy-Heparine

Heparin sodium salt (1.0 g, Mn=12000, activity=195 IU/mg, Porcine Intestinal Mucosa, obtained from Merck Biosciences, Germany) was dissolved in water and passed through a Dowex 50X8 (H+) column, followed by dialyzing (MW cut-off=12000-14000) against water and lyophilization to obtain heparin (0.95 g). The reducing end of heparin was oxidized with iodide (0.2 g) in 20% aqueous methanol solution (25 mL) for 6 h at room temperature. The reaction solution was added to ethanol containing 4% by weight potassium hydroxide (50 mL). The resulting white precipitate was filtered, dissolved in water and dialyzed (MW cut-off=12000-14000). Oxidized heparin was obtained after lyophilization The oxidized heparin was subsequently dissolved in water and passed through a Dowex 50X8 (H+) column followed by freeze drying to obtain the lactone-heparin (0.74 g). A 10-fold molar excess of UPy5 (45 mg) was dissolved in DMF (2 mL) and subsequently added to lactone-heparin (200 mg) dissolved in DMF (10 mL). The reaction was stirred for 16 h at 80° C. The reaction mixture was concentrated in vacuo followed by dissolving in water. The dilute reaction mixture was subsequently passed through a Dowex 50X8 (H+) column. The eluate was extensively dialyzed against water, followed by lyophilization resulting in heparin terminally functionalized with a 4H-unit.

Examples of Processing of the Bioresorbable Supramolecular Material

Example 26

The polymer of example 14 was processed via different techniques into several scaffolds that can be issued for tissue-engineering. Films were made by solvent casting from THF solution or via compression moulding (at approximately 20° C. above the melting temperature). Melt spinning (at a temperature of 90° C.) and electrospinning (from chloroform solution) were used to make fibres and meshes. Grids with a fibre width down to approximately 220 μm were produced via Fused Deposition Modelling (FDM) at temperatures just below 75° C.

Example 27

A bioactive hydrogel was obtained by dissolving the polymers of example 7 (4.3 g) and of example 14 (1.0 g) in THF (70 mL), followed by the gentle addition of 82 mL deionized water to the stirred polymer-solution. To this mixture was added Rhodamine B (100 mg). This mixture was concentrated at a rotavap until all THF was removed and a pink hazy hydrogel was obtained that showed orange fluoresence. The resulting hydrogel had elastic properties and displayed viscoelastic behavior.

Example 28

Bioactive materials were obtained by making three different peptide solutions by dissolving: (a) 4 mole % of the oligopeptide of example 18; (b) 4 mole % of the oligopeptide of example 19; and (c) both oligopeptides of examples 18 and 19 together (4 mole % of each peptide) in THF with 10-30% water. Subsequently, the polymer of example 8 was dissolved in THF. Bioactive blends were produced by mixing the peptide solutions and polymer solution. The resulting mixtures were drop cast on glass cover slips (diameter=1.5 cm; $1 \cdot 10^{-4}$ mmol peptide in the case of 4 mole % peptide and $2.4 \cdot 10^{-3}$ mmol polymer per cover slip) resulting in three different oligopeptide-loaded films: 28a, 28b, and 28c. Most of the times, a slight precipitate was visible. The blends on the glass cover slips were dried in vacuo for 2-3 days at 35-40° C. This resulted in bioactive films.

Example 29

Bioactive materials were obtained by first drop casting the polymer of example 14 from THF on glass cover slips (diameter=1.5 cm). Subsequently, three different solutions were made by dissolving: (a) the oligopeptide of example 18; (b) the oligopeptide of example 19; and (c) both oligopeptides of examples 18 and 19 together in THF with 10-30% water. Peptide concentrations of 1, 2, 4 or 8 mole % were used. These solutions were drop cast on the dried polymer film. Most of the times, a slight precipitate was visible. Typically, on one cover slip $1 \cdot 10^{-4}$ mmol peptide in the case of 4 mole % peptide and $2.4 \cdot 10^{-3}$ mmol polymer were loaded. The blends on the glass cover slips were dried in vacuo for 2-3 days at 35-40° C., resulting in three different oligopeptide-loaded films: 29a, 29b, and 29c, that all contained different loadings of the oligopeptides. The samples were sterilized under UV for at least 3 hours, prior to use in cell adhesion and spreading experiments or in extraction experiments in vitro.

Example 30

A bioactive material consisting of the polymer of example 14 and the UPy-biotin of example 21 was made via the following method. The polymer of example 8 (0.80 g) was dissolved in THF (2 mL). The white powder obtained in example 21 (34 mg) was added to the THF solution which was subsequently shaken for a few minutes and spin coated (3500 rpm, 15 s) or drop cast on cleaned glass cover slips (diameter=1.5-2.2 cm). The samples were dried for 1 hour in vacuo at room temperature. This resulted in UPy-biotin containing bioactive films.

Example 31

A polyethylene glycol with 4H-units was prepared as described in Example 9 (12 g), but now after 10 minutes stirring at 140° C., L-ascorbic acid (0.66 g) was added to the polymer melt while stirring the mixture. After 5 minutes stirring at 140° C., the polymeric melt was poured in a mould and cooled down to room temperature. The resulting ascorbic acid containing supramolecular polyethylene glycol was obtained as a hard white material that slowly released the ascorbic acid upon immersing the material in water buffered at pH=7.2 with HEPES (50 mM).

Example 32

Telechelic hydroxy terminated polycaprolacton with a molecular weight of 1250 D (3.04 g) and telechelic hydroxy terminated PEO-3000 (5.67 g) were heated together in vacuo in a 3-neck flask to 120° C. for 30 minutes, followed by the addition of 5 drops dibutyltindilaurate and UPy1 (2.54 g). This heterogeneous reaction mixture was subsequently stirred with a mechanical stirrer under an argon atmosphere and heated to 150° C. After 20 minutes stirring at 150° C., finely grinded 4-acetaminophenol (309 mg) was added and stirring was continued for 5 minutes at 140° C. After cooling down, a hard semi-flexible white material was obtained that contained 2.7% by mass of the bioactive 4-acetaminopheniol. Immersing the material in water buffered at pH=7.2 with HEPES (50 mM) resulted in a slow release of the bioactive compound.

Examples of Biocompatibility, Biodegradability and Bioactivity of Bioresorbable Supramolecular Material Example 33

Cell culture in vitro: 3T3 mouse fibroblasts were cultured on a 1:1 mixture of Ham's F-12 and Dulbecco's Modified Eagle's Medium with 10% Fetal Bovine Serum (FBS). They were cultured in a humidified incubator at 37° C. and 5% $CO_2$. Before seeding of the cells on the materials, they were washed twice with PBS solution. Then they were trypsinized with a trypsin-EDTA solution (it was checked with FACS measurements that cells contain the $\alpha_5\beta_1$ integrins irrespective of treatment of the cells with trypsin-EDTA or with EDTA solution), washed with PBS and counted after trypan blue staining in a Neubauer counting chamber. The cells were seeded in the culture medium (with or without FBS supplemented, as indicated) on the films. The passage of the cells was always between 10 and 80 and the viability of the cells was always above 97%.

Cell adhesion and cell spreading experiments: 3T3 mouse fibroblasts ($5·10^4$ cells/cm$^2$) were seeded on the cover slips with the supramolecular bioactive materials of example 29 (29a, 29b and 29c) and on cover slips with the polymer of example 14, on the bottom of a polystyrene culture dish and on glass in 200 μL medium (with or without FBS, as indicated). They were incubated for 5 minutes at room temperature, after which 1 mL medium (with or without FBS, as indicated) was added. During 1 or 2 days of culturing in a humidified incubator at 37° C. and 5% $CO_2$, they were studied with optical microscopy.

When the mouse 3T3 fibroblasts were cultured on the different bioactive blends (29a, 29b, 29c; in all cases 4 mole % of peptide was mixed with the polymer solution prior to preparing the films) and on the polymer of example 14 for 2 days in the absence of FBS (Fetal Bovine Serum) to prevent cell adhesion via absorbed serum proteins, aspecific adhesion but hardly any cell spreading, was already visible after 3 hours on all samples. However after 1 day, additional cell spreading and the highest degree of cell adhesion was observed for cells seeded on blend 29c which might indicate the possible synergistic effect of the two UPy-peptides. On the film of 29a some cells adhered and spread after 1 day, but less efficient as on blend 29c. Also less cells spread on mixture 29b after 1 day. This is proposed to be due to the fact that PHSRN is a synergistic sequence. These findings for the different films remained unchanged even after 2 days, as illustrated in FIG. 1.

Example 34

Inhibition experiments as a comparative study: 3T3 mouse fibroblasts ($4·10^5$ cells/mL medium without FBS) were incubated at room temperature for 15 minutes with soluble GRGDS peptides (0.3 mM in medium without FBS). After this incubation step the cells ($6·10^4$ cells/cm$^2$) were seeded on the bioactive material 28c (containing 4 mole % of each peptide) in 250 μL medium without FBS. In the case of the control the cells ($6·10^4$ cells/cm$^2$) were not pre-incubated with these soluble GRGDS peptides. After seeding of the cells, they were incubated for 5 minutes at room temperature. Then 1 mL medium without FBS was added. After 1 day of culturing in a humidified incubator at 37° C. and 5% $CO_2$, they were studied with optical microscopy which showed that without incubation of the cells with soluble GRGDS peptides, the cells adhered and spread out on film 28c after 1 day. However after incubation of the cells with the soluble GRGDS peptides hardly any adhesion and spreading could be detected on film 24c after 1 day. This indicates that the cell binding might be integrin mediated.

Example 35

Cell binding strength and cell spreading reversibility experiments: Trypsin experiments were performed after 1 day of culturing the 3T3 mouse fibroblasts ($5·10^4$ cells/cm$^2$) at 37° C. and 5% $CO_2$ on three different set-ups: on film 28c (containing 4 mole % of each peptide) without FBS added, on film 28c (also containing 4 mole % of each peptide) in the presence of FBS, and on the bottom of the polystyrene culture dish in the presence of FBS (PS+FBS). They were all incubated in a trypsin-EDTA solution at room temperature for 30 seconds and 30 minutes. After removal of the trypsin-EDTA solution the cells were washed twice with PBS solution. The cells that remained after these washings were incubated again in a humidified incubator at 37° C. and 5% $CO_2$ for 1 day in cell culture medium without FBS. During the whole process the cells were followed with optical microscopy.

The cells cultured on blend 28c without FBS look similar as cells cultured on blend 28c or on the bottom of a polystyrene (PS) culture dish in the presence of FBS after 1 day of incubation. These results indicate that the peptides facilitate cell adhesion and spreading in a comparable manner as the extracellular matrix (ECM) proteins that are present in the FBS. Differences, however, can be found in cell binding strength experiments using trypsin-EDTA. After 30 seconds of incubation with trypsin-EDTA, the cells on blend 28c with FBS and on the PS with FBS were completely detached. These cells were subsequently washed off the plates leaving behind some floating single cells. On the contrary, even after 30 minutes of incubation with trypsin-EDTA the cells on blend 28c in the absence of FBS were still adhered and hardly any floating cells were observed. After removal of the trypsin-EDTA and washing of the fibroblasts, they could spread again on blend 28c without FBS when incubated for 1 additional day, suggesting that the UPy-peptides can act in a reversible fashion. These trypsin experiments indicate that the new supramolecular materials approach affords strong binding, but that the mechanism of binding is sensitive for competitive ECM proteins.

Example 36

In-vivo implantations: Four different solution cast films were prepared: a bioactive film containing 4 mole % of the peptide of example 18 and the polymer of example 14 (i.e. example 36a), a bioactive film containing both 4 mole % of the peptide of example 18 and 4 mole % of the peptide of example 19 and the polymer of example 14 (i.e. example 36b), a bare polymer film consisting of the polymer of example 14 (i.e. example 36c) and a bare polymer film consisting of the polymer of example 8 (i.e. example 36d). In this case the films were not drop cast on cover slips, but on petri dishes. The resulting polymer films had a diameter of 6 mm and were approximately 0.4 mm thick. They were all subcutaneously implanted in duplicate into male Albino Oxford (AO) rats. The implants with the surrounding tissue were explanted after 2, 5, 10, 21 and 42 days of implantation and were embedded in plastic (Technovit 7100 cold curing resin based on hydroxyethylmethacrylate (HEMA), Kulzer Histo-Technik) The samples were stained with toluidine blue for histological examination with optical microscopy.

The differences observed after in-vivo implantation between both supramolecular materials are striking. At day 5 the cellular infiltration was very mild for polymers of examples 14 and 8 and a small fibrous capsule had been formed reflecting the inert and adhesive characteristics of the materials. However, in the case of blends 36a and 36b vascularization and infiltration of macrophages was observed, which might be due to the presence of the peptides that could recruit cells through integrin binding. Another remarkable difference was the fact that in the case of blend 36a and 36b already after 5 days large giant cells were budding into the material from the interface, which indicates that the UPy-GRGDS and probably the UPy-PHSRN peptides may not only play a part in the signalling and infiltration of macrophages but also in their fusion to giant cells.

Figure 2:
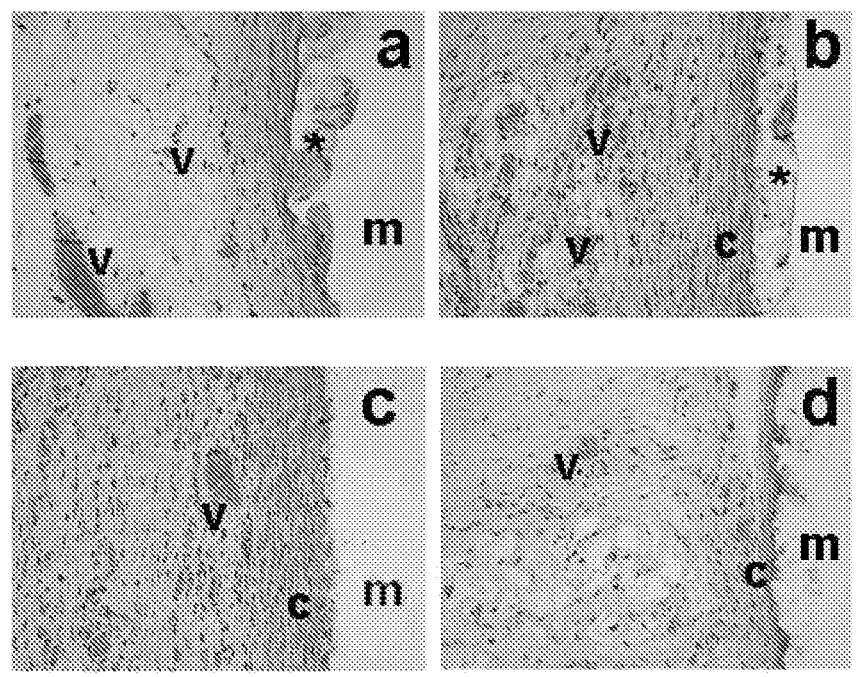
FIG. 2 shows in-vivo behaviour of the supramolecular bioactive materials: Solution-cast supramolecular bioactive films of examples 36a (FIG. 2a) and 36c (FIG. 2b), and the bare polymers of examples 14 (FIG. 2c) and 8 (FIG. 2d) were subcutaneously implanted in male AO rats. The films and surrounding tissue are shown after 21 days of implantation. The samples were stained with toluidine blue for histological examination. The magnifications are 200 times. The material is indicated with m. The fibrous capsule is shown with c. Blood vessels are indicated with v. The giant cells that are budding into the material from the interface are indicated with an asterisk (*).

Giant cells were not detected in the bare polymers and the cellular response was negligible up to 42 days. However, the tissue response for both bioactive blends 36a and 36b became even more active after 10 days and degradation of the polymer was shown by phagocytotic activity of giant cells present in the surrounding tissue. The giant cells at the interface still did not show any phagocytotic behaviour up to 42 days, although ongoing degradation was observed after 42 days. The results after 21 days of implantation are visible in FIG. 2. The differences between the bioactive blends and the bare polymers are clear. The bare polymers of examples 8 and 14 also behave different. After 42 days the polymer of example 8 is degraded and could hardly be found back in the animal, this in contrast with the polymer of example 14 that was hardly degraded. Also the fibrous capsule in the case of polymer of example 8 is much thinner than in the case of polymer of example 14.

Example 37

Degradation studies in vitro: The degradation behaviour of films of the polymer of example 14 was studied in buffer in the presence of lipase enzymes, via mass measurements (the dry mass of the samples was measured on a Sartorius microbalance), differential scanning calorimetry (DSC) and size exlusion chromatography (SEC) after rinsing the samples three times with water and drying them at 40° C. for 1.5 hours.

Films of the polymer of example 14 were made via drop casting from chloroform solution and dried in vacuo at 35-40° C. for 2-3 days prior to use. Samples were shaken in a lipase (from *Thermomyces lanuginosus*, Aldrich) containing solution which was diluted 1000 times with PBS solution supplemented with sodiumazide (0.05%) at 37° C. for 23 days. During enzymatic degradation of polymer 14 with the lipase from *Thermomyces lanuginosus* chain scission was demonstrated with gel permeation chromatography techniques. After 15 days already 90% mass loss was found.

Example 38

The extraction of the peptide of example 18 and the peptide GRGDS without a UPy-unit out of films of example 29a was investigated with LC-MS measurements. The amount of peptide that was mixed in the polymeric materials is in both cases 4 mole %. Calibration was performed by quantification of one fragment of the parent ion ($MS^2$) of the peptides using different concentrations of the peptides. The surface area of the corresponding peak (in the total ion count) was calculated with the ICIS algorithm. The extraction experiments were performed as follows: the film was incubated at 37° C. for 5 minutes in 1 mL water, then the water was removed and the concentration of peptide was measured with the described LC-MS procedure (time-point: 5 minutes); another 1 mL water was added to the film which was subsequently incubated again for 5 minutes at 37° C. followed by removal of the water which was analysed with the LC-MS method (time-point: 10 minutes); another 1 mL water was added to the film and the sample was incubated for 10 minutes at 37° C. followed by removal of the water which was analysed with the LC-MS method (time-point: 20 minutes); incubation at 37° C. in another 1 mL water for 20 minutes, followed by removal of the water which was analysed with the LC-MS method (time-point: 40 minutes); and incubation at 37° C. in another 1 mL water for 40 minutes, followed by removal of the water which was analysed with the LC-MS method (time-point: 80 minutes).

These extraction experiments show that dissolution of GRGDS without a UPy-moiety proceeds extremely fast in water at 37° C.; within 5 minutes almost all of the peptide is dissolved (Table 1). After 80 minutes of incubation at 37° C. in a total volume of 5 mL water the whole quantity of GRGDS peptide (105%) is dissolved. When a film with 4 mole % GRGDS is incubated for 2 hours at 37° C. in 1 mL water also the whole amount of GRGDS peptide (101%) is dissolved. The extraction of UPy-GRGDS with water from the film of example 29a is a slower process. After incubation at 37° C. of film of example 29a containing 4 mole % of UPy-GRGDS for 80 minutes in a total volume of 5 mL water ultimately 76% of the UPy-peptide is dissolved (Table 1). However, if this film with 4 mole % UPy-GRGDS is incubated for 2 hours in 1 mL water at 37° C. 64% of the UPy-GRGDS peptide is dissolved. This indicates that the UPy-unit is important for the tuneable but dynamic binding of the peptide to the polymer.

TABLE 1

Extraction experiments on films of polymer of example 14 with UPy-GRGDS (film 29a) or GRGDS: The GRGDS peptide is extracted much faster in water than the UPy-GRGDS peptide.

| time (min) | extraction GRGDS (%) | extraction UPy-GRGDS (%) |
|---|---|---|
| 5 | 91 | 39 |
| 10 | 97 | 60 |
| 20 | 100 | 76 |

Example 39

Stability test on bioactive materials m: To test the stability of the bioactive films of examples 29a, 29b and 29c in medium the whole cell adhesion and cell spreading experiment was repeated of example 33, but this time the samples were incubated in medium without FBS (1 mL) in a humidified incubator at 37° C. and 5% $CO_2$ for 3 hours, prior to seeding of the cells on the polymers. After this incubation step, the samples were washed two times with PBS solution and the cells were cultured in medium without FBS on these films in a humidified incubator at 37° C. and 5% $CO_2$ for 1 day. The cells were studied with optical microscopy. This resulted in similar adhesion and spreading patterns as shown before (cf. Figure example 33).

Example 40

Heparin-Containing Supramolecular Hydrogel

Aqueous solutions of acrylamide (1.3 mL; 40% w/v in water) and bisacrylamide (0.6 mL; 2% w/v in water) were mixed. This mixture was diluted with tris(hydroxymethyl)aminomethane-buffer (Tris, 1.2 mL; 0.4 M Tris-HCl, pH 8.8) and water (1.5 mL) followed by the addition of the 4H-unit functionalized heparin of example 25 (123 mg). This mixture was heated to 80° C. and subsequently, UPy6 (48 mg) dissolved in acrylamide (0.20 mL) was added. The mixture was polymerized after the addition of ammoniumpersulfate (50 μL; endconcentration 0.1%) and N,N,N',N'-tetramethylethylenediamine (TEMED, 2.5 μL; endconcentration 0.1%), resulting in a 12% acrylamide gel containing functionalized with 4H-units and containing 2% by weight of the bioactive component according to example 24.

Example 41

UV-Cured Supramolecular Coating

Polymer XI (2.5 g) and UPy6 (1.5 g) were dissolved in hydroxyethyl acrylate (HEA, 10 g) together with tetraethyleneglycol diacrylate (TEGDA, 1.0 g), Irgacure 907™ (150 mg, obtained from Ciba, Switzerland) at 80° C. Then a 100 μm film was mechanically drawn on a glass substrate and UV-cured under a nitrogen atmosphere with a Fusion F600 D-bulb ($I_0$=5 W/cm$^2$) with a belt speed of 10.4 m/min, equivalent to a radiation time of 0.3 s. A clear coating was obtained with good mechanical properties.

The invention claimed is:

1. An implant for biomedical applications or a biomedical coating composition comprising a supramolecular material that comprises:
   (a) a polymer comprising at least three 4H-units; and
   (b) a biologically active compound;
   wherein the supramolecular material comprises 50.00-99.99 percent by weight of the polymer and 0.01-50.00 percent by weight of the biologically active compound, based on the total weight of the supramolecular material; and
   wherein the 4H-units have the general formula (3) or formula (4) and tautomers thereof:

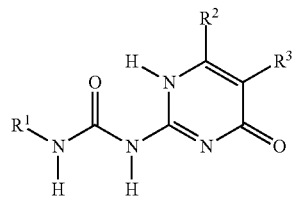

(3)

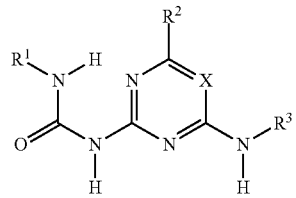

(4)

wherein X is nitrogen atom or a carbon atom bearing a substituent $R^8$ and wherein $R^1$, $R^2$, $R^3$ and $R^8$ are independently selected from the group consisting of:
(i) hydrogen;
(ii) $C_1$-$C_{20}$ alkyl;
(iii) $C_6$-$C_{12}$ aryl;
(iv) $C_7$-$C_{12}$ alkaryl;
(v) $C_7$-$C_{12}$ alkylaryl;
(vi) polyester groups having the formula (5):

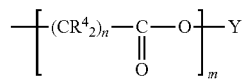

(5)

wherein $R^4$ and Y are independently selected from the group consisting of hydrogen and $C_1$-$C_6$ linear or branched alkyl, n is 1 to 6, and m is 10 to 100;
(vii) $C_1$-$C_{10}$ alkyl groups substituted with 1-4 ureido groups according to the formula (6):

$$R^5\text{—NH—C(O)—NH—} \quad (6)$$

wherein $R^5$ is selected from the group consisting of hydrogen and $C_1$-$C_6$ linear or branched alkyl; and
(viii) polyether groups having the formula (7):

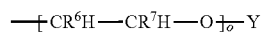

(7)

wherein $R^6$, $R^7$ and Y are independently selected from the group consisting of hydrogen and $C_1$-$C_6$ linear or branched alkyl and o is 10 to 100;
wherein the at least three 4H-units are bonded to the backbone of the polymer via $R^1$ and $R^2$, while $R^3$ represents a side chain according to (i)-(viii), or via $R^1$ and $R^3$, while $R^2$ represents a side chain according to (i)-(viii); and
wherein the polymer is derived from polymers having two terminal hydroxyl groups, the polymer being selected from the group consisting of polyethers, polyesters, polycarbonates, polyorthoesters, and copolymers from these polymers.

2. The implant or coating according to claim 1, wherein the polymer is derived from the group consisting of polyesters, polycarbonates, and copolymers from these polymers.

3. The implant or coating according to claim 1, wherein the polymer is derived from the group consisting of polycaprolactone, polylactide, polyglycolide, poly(trimethylene) carbonate, poly(1,6-hexanediol) carbonate, and copolymers from these polymers.

4. The implant or coating according to claim 1, wherein the biologically active compound is selected from the group consisting of antimicrobial agents, anti-viral agents, anti-tumor agents, antithrombogenic agents, hormones, immunogenic agents, growth factors, dyes, fluorescent dyes, contrast agents, nucleic acids, lipids, lipopolysaccharides, saccharides, polysaccharides, vitamins, peptides, oligopeptides, proteins, apatite, hydroxyapatite, anaesthetics, muscle relaxants, and corticosteroids.

5. The implant or coating according to claim 1, wherein the implant or coating is obtained by a processing method selected from freeze drying, particulate leaching, electrospinning, spinning, and fused deposition modelling.

6. The implant or coating according to claim 1, wherein component (a) comprises three to fifty 4H-units.

7. The implant or coating according to claim 1, wherein component (a) has a $M_n$ of 100 to 100,000.

8. The implant or coating according to claim 1, wherein the biologically active compound is selected from the group consisting of antithrombogenic agents, lipopolysaccharides, saccharides, polysaccharides, heparin, heparin complexes, heparin-analogues and molecules comprising a sulfonated glycosaminoglycan moiety.

9. The implant or coating according to claim 1, wherein component (b) is not modified with a 4H-unit.

10. A medical device comprising the implant or coating according to claim 1.

11. The medical device according to claim 10, wherein the medical device is selected from the group consisting of stents, catheters, implants, and prostheses.

12. A tissue-engineered material comprising the implant or coating according to claim 1.

13. A method of engineering tissue comprising incorporating an implant or coating according to claim 1 into a scaffold.

* * * * *